United States Patent [19]
Granato et al.

[11] Patent Number: 6,021,664
[45] Date of Patent: Feb. 8, 2000

[54] AUTOMATED GROUNDWATER MONITORING SYSTEM AND METHOD

[75] Inventors: Gregory E. Granato, Upton, Mass.; Kirk P. Smith, Mason, N.H.

[73] Assignee: The United States of America as represented by the Secretary of the Interior, Washington, D.C.

[21] Appl. No.: 09/015,214

[22] Filed: Jan. 29, 1998

[51] Int. Cl.⁷ .......................... G01N 11/00; E21B 49/00; E21B 47/00; E02B 11/00

[52] U.S. Cl. ..................... 73/53.01; 73/152.18; 166/264; 210/170

[58] Field of Search .............................. 73/53.01, 152.29, 73/152.18, 863.01, 864.34, 49.2; 166/264, 68, 105, 107, 369; 175/59; 417/44.11; 210/170, 198.2

[56] References Cited

U.S. PATENT DOCUMENTS

| | | | |
|---|---|---|---|
| 4,489,779 | 12/1984 | Dickinson et al. | 166/64 |
| 4,717,473 | 1/1988 | Burge et al. | 210/170 |
| 5,224,389 | 7/1993 | Jensen et al. | 73/863.01 |
| 5,259,450 | 11/1993 | Fischer | 166/68 |
| 5,264,368 | 11/1993 | Clark et al. | 436/3 |
| 5,293,931 | 3/1994 | Nichols et al. | 166/54.1 |
| 5,432,709 | 7/1995 | Vollweiler et al. | 702/32 |
| 5,490,561 | 2/1996 | Cardoso-Neto et al. | 166/264 |
| 5,496,733 | 3/1996 | Spandau et al. | 436/52 |
| 5,553,492 | 9/1996 | Barrett et al. | 73/152.29 |

*Primary Examiner*—Hezron Williams
*Assistant Examiner*—Jay L. Politzer
*Attorney, Agent, or Firm*—E. Philip Koltos

[57] ABSTRACT

A method of monitoring the quality of water at a ground water sampling site without human intervention. Water at the sampling site is purged until at least one preselected purge criterion is satisfied. At least one water quality attribute is automatically measured at the sampling site, and the quality of water at the site is determined based on the measured water quality attribute. The method is performed by a system including a control unit which, in accordance with a computer program, controls the taking of water quality attribute measurements at the sampling site. The control unit may be equipped with a port for downloading data to a technician on site and with a transceiver for communicating data to a base station via a communications network.

46 Claims, 20 Drawing Sheets

U.S. GEOLOGICAL SURVEY TOXIC SUBSTANCES HYDROLOGY PROGRAM RESEARCH SITE, MASSACHUSETTS MILITARY RESERVATION, CAPE COD, MASSACHUSETTS

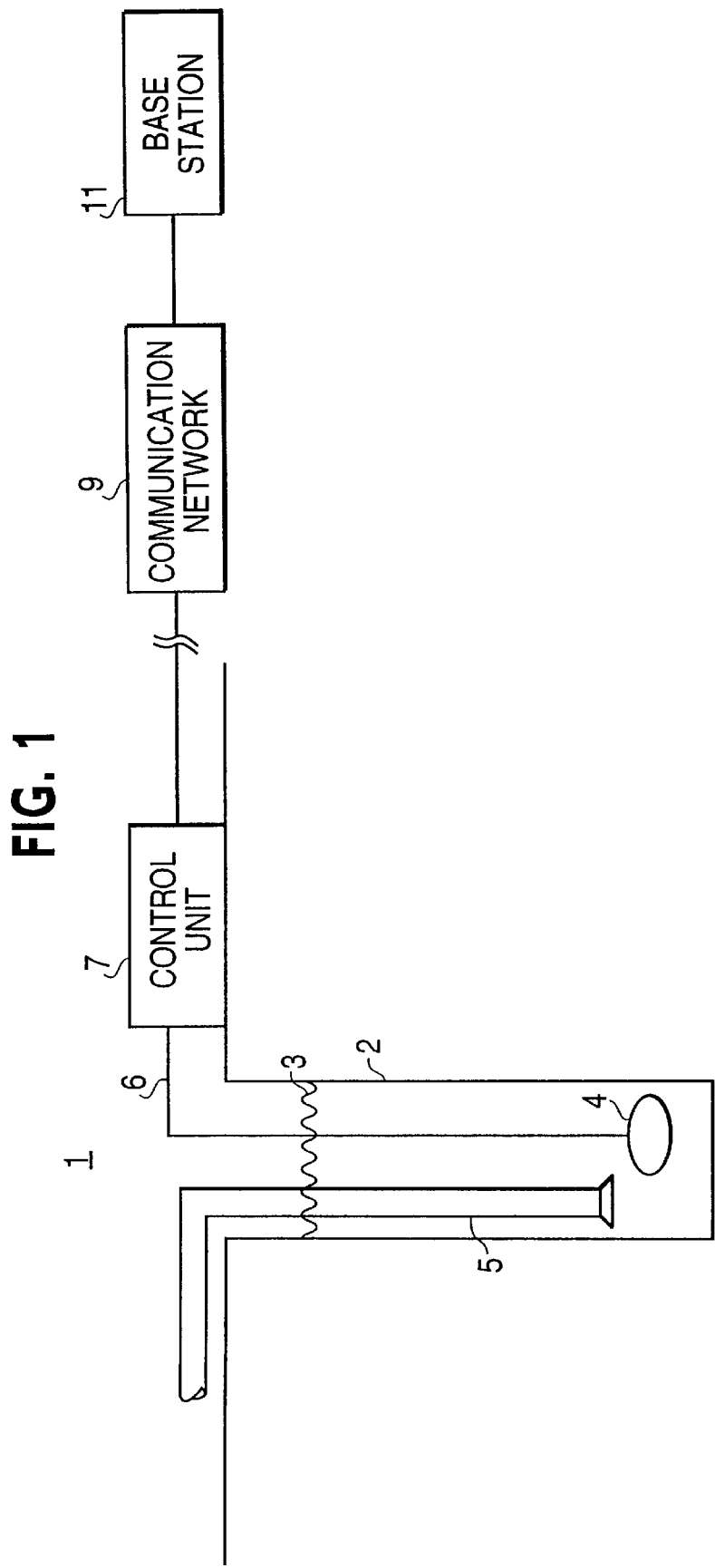

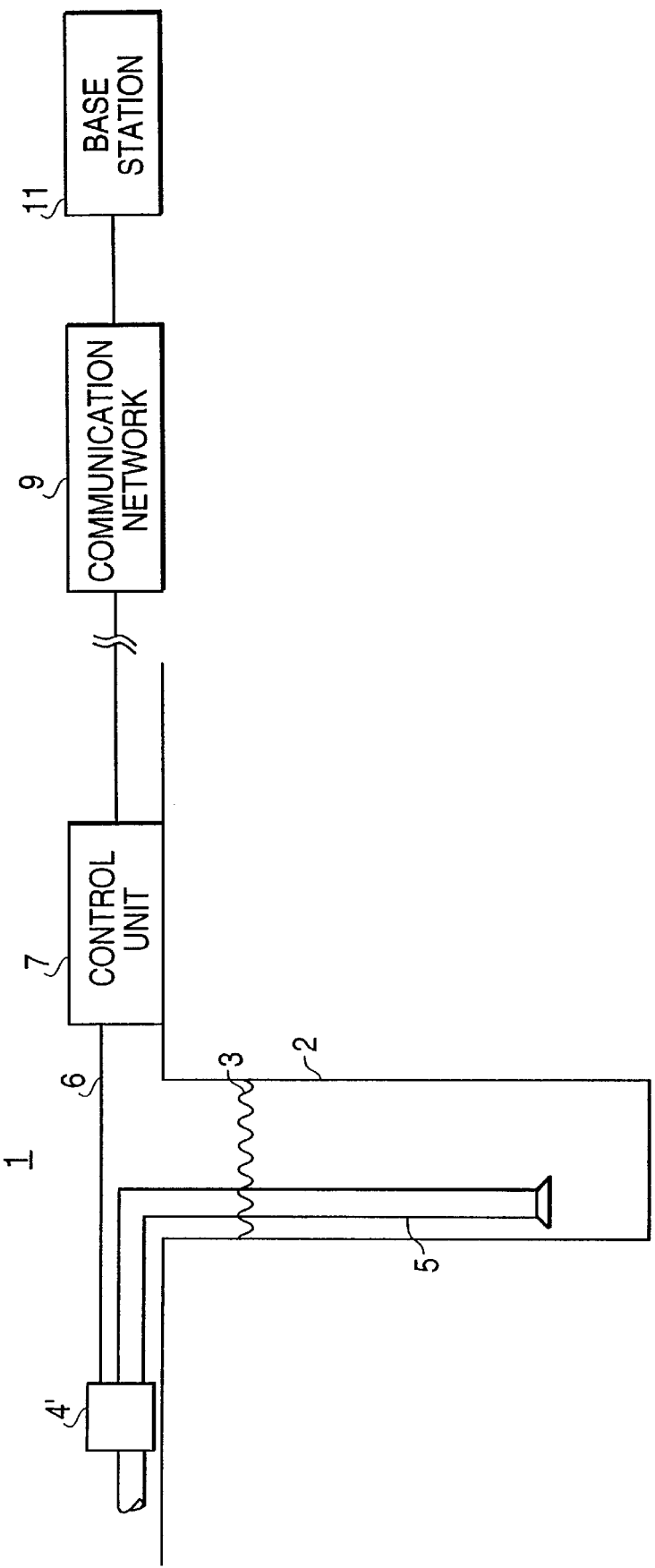

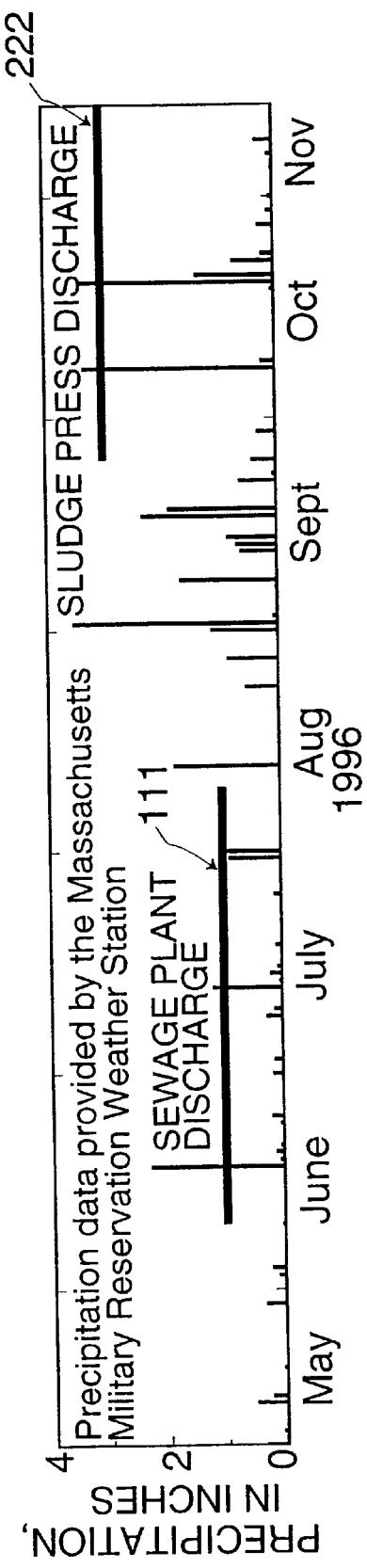
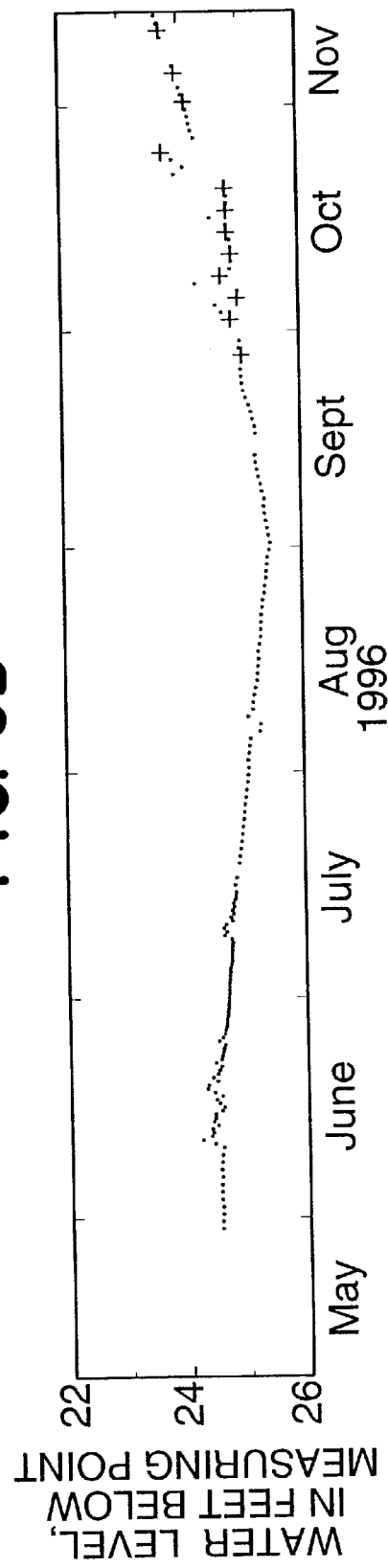
FIG. 9A
FIG. 9B

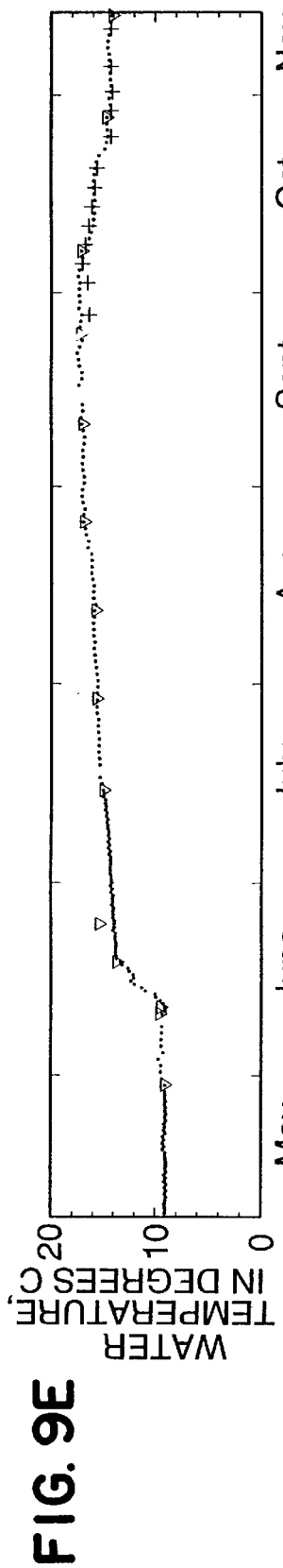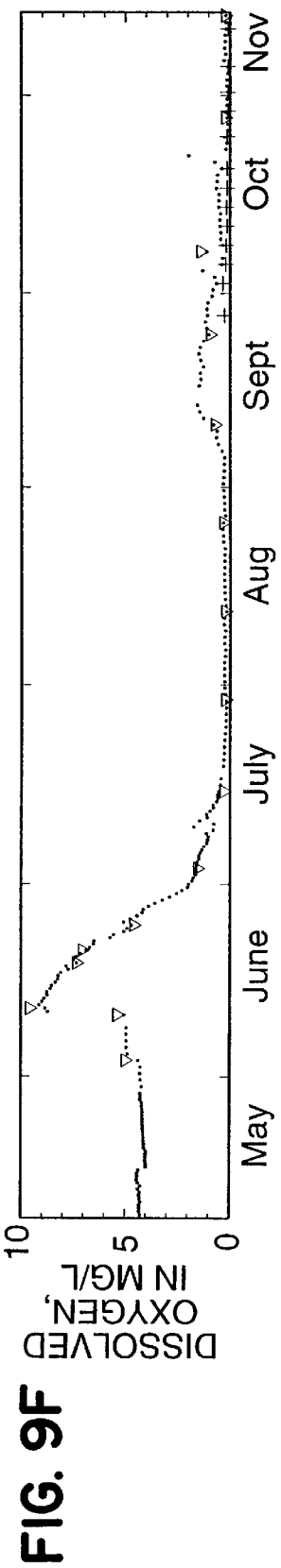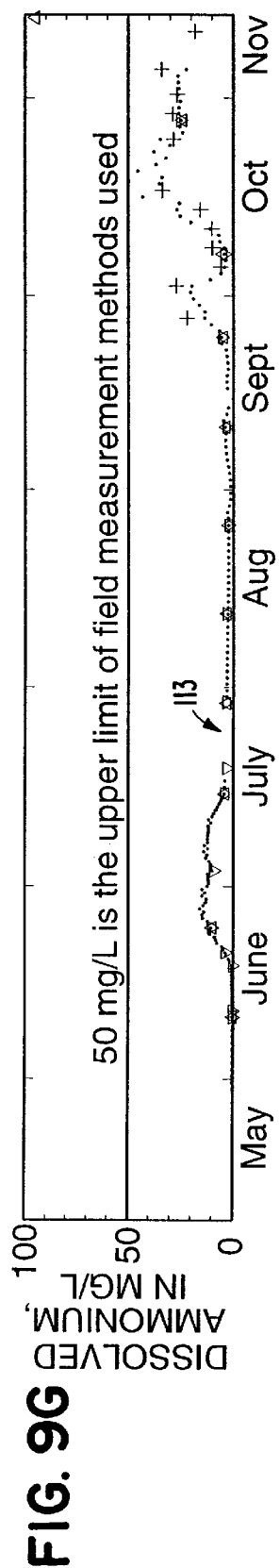

FIG. 10

| CONSTITUENTS AND PROPERTIES | EFFLUENT SAMPLES, FROM SEWAGE PLANT DECOMMISSIONING | | | | GROUND WATER SAMPLES | | | |
|---|---|---|---|---|---|---|---|---|
| | CLARIFIER (1) | IMHOFF TANK (2) | SLUDGE PRESS EFFLUENT (3) | (4) | PRE-RELEASE (5) | (6) | POST-RELEASE (7) | (8) |
| COLLECTION DATE | 06/10/96 | 06/24/96 | 09/27/96 | 10/07/96 | 05/09/96 | 06/24/96 | 08/26/96 | 11/13/96 |
| SPECIFIC CONDUCTANCE, μS/CM AT 25°C | 226 | 838 | 5300 | 3220 | 178 | 520 | 608 | 6070 |
| TEMPERATURE, °C | 14.2 | 15.0 | 17.8 | 16.2 | 9.1 | 13.9 | 16.9 | 14.1 |
| DISSOLVED OXYGEN | AERATED | AERATED | AERATED | AERATED | 4.27 | 5.09 | 0.31 | 0.18 |
| pH, IN STANDARD UNITS | 7.3 | 6.7 | 11.4 | | 5.8 | 6.2 | 5.7 | 8.0 |
| DISSOLVED SOLIDS, SUM OF CONSTITUENTS | 129 | 460 | 2310 | | 124 | 307 | 395 | 3190 |
| DISSOLVED SOLIDS, RESIDUE ON EVAPORATION | 136 | 328 | 3220 | | 110 | 268 | 445 | 3260 |
| ALKALINITY (AS $CaCO_3$) | 53 | 303 | 391 | | 13 | 111 | 40 | 132 |
| HARDNESS (AS $CaCO_3$) | 45 | 120 | 2000 | | 32 | 69 | 120 | 2500 |
| CHLORIDE (Cl) | 20 | 54 | 1200 | | 17 | 38 | 46 | 1900 |
| BROMIDE (Br) | <0.01 | <0.01 | 0.45 | | 0.01 | <0.01 | 0.02 | — |
| SULFATE ($SO_4$) | 13 | 11 | 17 | | 11 | 14 | 14 | 43 |
| FLUORIDE (F) | 0.6 | 0.8 | 0.8 | | 1. | 1.3 | 0.9 | 1.5 |
| CALCIUM (Ca) | 15 | 40 | 810 | | 9.8 | 20 | 39 | 1000 |
| MAGNESIUM (Mg) | 1.9 | 5.4 | 0.14 | | 1.8 | 4.7 | 6.3 | 1.5 |
| SODIUM (Na) | 23 | 55 | 34 | | 17 | 46 | 50 | 31 |
| POTASSIUM (K) | 5.2 | 15 | 9.3 | | 6.3 | 21 | 16 | 8.1 |
| IRON (μg/L AS Fe) | 81 | 1200 | 18 | | 23 | 25 | 10 | 1300 |
| MANGANESE (μg/L AS Mn) | 39 | 5.4 | 3.0 | | 10 | 10 | 21 | 22 |
| SILICA ($SiO_2$) | 5.2 | 18 | 4.1 | | 9.7 | 13 | 19 | 1.4 |
| AMMONIA AND AMMONIUM (AS N) | 0.84 | 36 | — | 17 | 0.03 | 9.8 | 2.0 | 95 |
| NITRITE ($NO_2$ AS N) | 0.08 | 0.01 | — | 0.05 | <0.01 | 0.06 | 0.01 | 0.52 |
| NITROGEN, AMMONIA AND ORGANIC (AS N) | 1.7 | 37 | — | 26 | 0.4 | 10 | 2.4 | 100 |
| NITRITE AND NITRATE ($NO_2$ + $NO_3$ AS N) | 1.3 | 0.07 | — | 2.0 | 7.3 | 14 | 36 | 0.71 |
| PHOSPHORUS (P) | 2.3 | 9.5 | — | 0.12 | 3.0 | 2.2 | 5.8 | 0.15 |
| ORTHOPHOSPHATE ($PO_4$ AS P) | 2.2 | 10 | — | 0.01 | 3.2 | 2.5 | 5.7 | 0.01 |

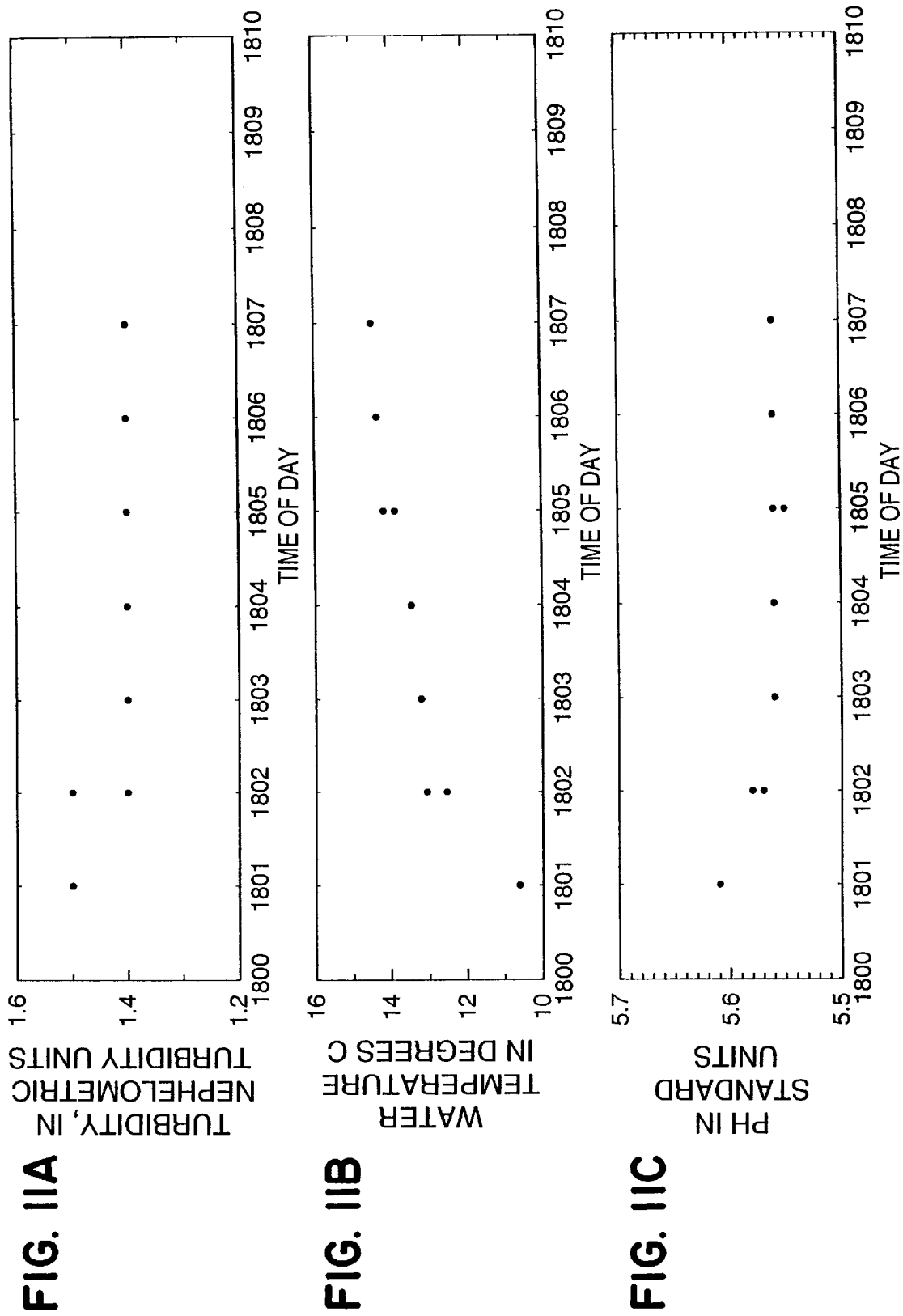

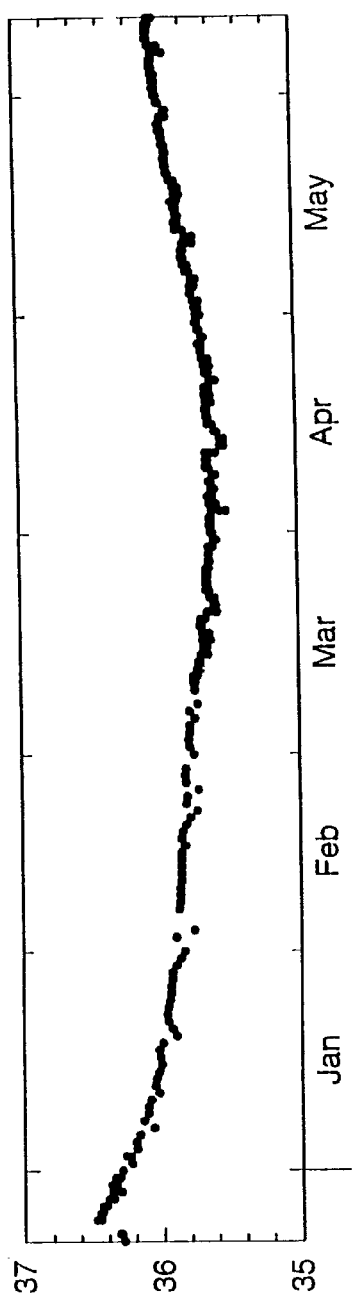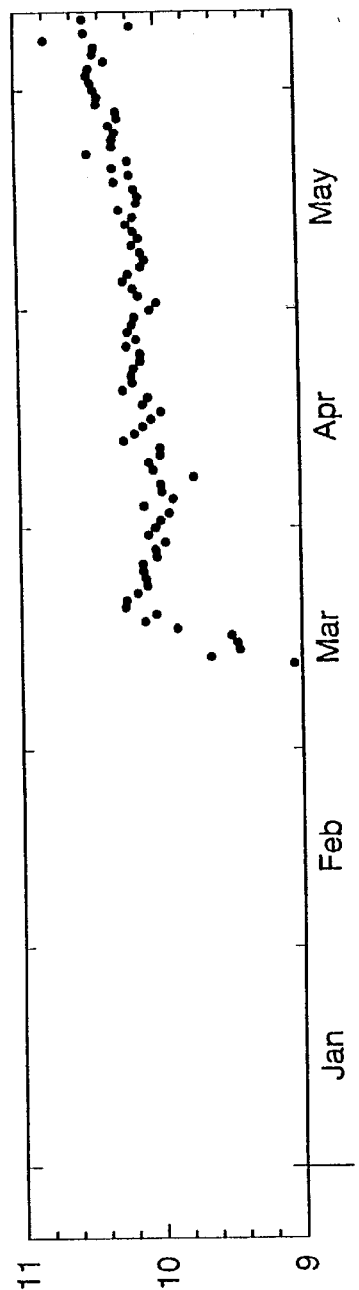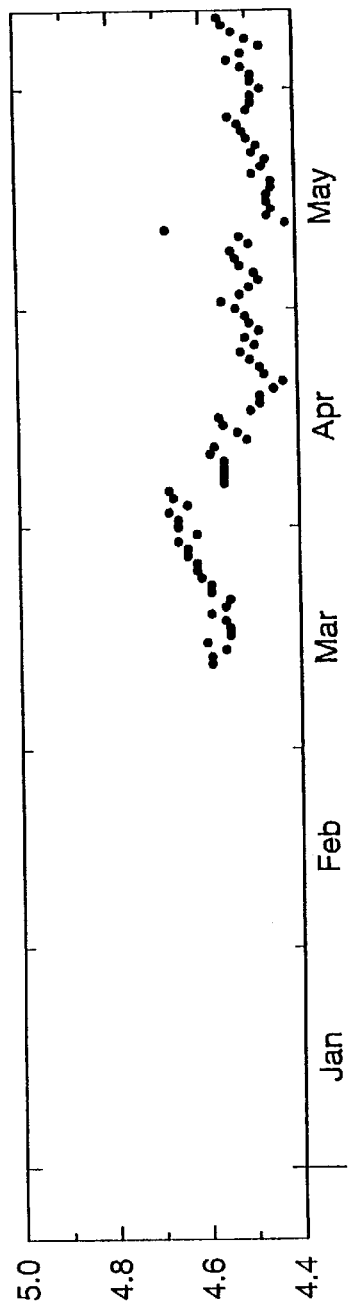

AUTOMATED GROUNDWATER MONITORING SYSTEM AND METHOD

BACKGROUND OF THE INVENTION

1. Field of the Invention

This invention generally relates to monitoring of water quality, and more particularly to an automated system for and method of monitoring the quality of water at one or more ground water sampling sites.

2. Description of the Related Art

Determining the quality of water by monitoring one or more of its properties and constituents is well known, and at present is generally accomplished by one of two methods.

The first method is a manual method in which a field technician is deployed to draw samples from a well. The samples are then tested on-site in accordance with established protocols or are transported to a laboratory for analysis. The following publications disclose manual methods of this type: Gilliam et al, *Groundwater Monitoring and Sample Bias*, Environmental Affairs Department, American Petroleum Institute, page 206, June 1983; Driscoll, *Groundwater and Wells,* 2nd edition, page 1108, 1986; and Koterba et al, "Ground-Water-Data-Collection Protocols and Procedures for the National Water-Quality Assessment Program—Collection and Documentation of Water-Quality Samples and Related Data," U.S. Geological Survey Open-File Report 95-399, page 113, 1995.

Manual methods for determining ground water quality have proven to be inherently burdensome and inefficient. For example, as noted in the article "Sampling Frequency for Monitoring the Actual State of Ground Water Systems," *Journal of Hydrology* Volume 180, pages 301–318, 1996 by Zhou, the necessity of having to deploy one or more field technicians to a site to retrieve test samples has proven to be economically unsound, and the costs associated therewith only tend to increase in proportion to the number of wells tested within a given sampling site.

Manual methods are undesirable also because personnel shortages, inclement weather, and other factors limit the frequency with which samples can be taken,—i.e., typically water samples can be tested only once or twice a month in areas having a high concentration of sites. Consequently, changes in water quality that take place over short periods of time, for example, due to surges of effluent and other contaminating influences into the water table, will often go undetected. Thus, manual methods are inherently unreliable as research tools. See the Zhou article noted above, as well as Johnson et al, "Reducing the Sampling Frequency of Groundwater Monitoring Wells", *Environmental Science and Technology*, Volume 30, no. 1, pages 355–358, 1996, for a more in-depth discussion of these and other drawbacks, and of various unsuccessful approaches which have been taken in an attempt to improve the inherent deficiencies of manual ground water quality monitoring methods.

The second method for monitoring water quality is an automated method employing passive techniques. According to this method, a data logger controls a probe in a well to make measurements from which water quality can be determined. Automated methods of this type are disclosed in the article "Automated Monitoring and Interactive Data Evaluation for a Gravel Aquifer in Central London," *Journal of Engineering Geology*, Volume 25, note 4, pages 351–358, 1992, by Evans.

Automated systems have, in other monitoring applications, outperformed their manual counterparts. Perhaps most notably, automated systems are less expensive to operate, mainly because use of a data logger relieves field technicians of the job of having to capture the samples to be tested. Automated systems also advantageously may be programmed to take a greater frequency of measurements as compared with measurements taken by manual methods. The data collected by such automated systems are often electronically stored, and thus have proven to be comparatively easier to use. All of these advantages translate into lower costs, and a broader statistical basis from which water quality at a given site can be determined.

Some automated systems have been equipped with diagnostic feedback, which plays a pivotal role in increasing system reliability. For these and other advantages see, for example, Fink et al, "Computerized System Simplifies Well Testing/Monitoring", *World Oil*, Volume 216, No. 6, pages 109–110, 1995; Church et al, "Effectiveness of Highway-Drainage Systems in Preventing Contamination of Ground Water by Road Salt, Route 25, Southeastern Massachusetts-Description of Study Area, Data Collection Programs, and Methodology," U.S. Geological Survey Open-File Report 96-317, 1996; Igarashi et al, "Continuous Monitoring of Groundwater Radon for Evaluating Chemical and Structural Properties and Fluid Flow Variations of Shallow Aquifer Systems," *Journal of Science of the Hiroshima University* 10, No. 2, pages 349–356, 1995; Riley et al, "Automated Water Quality Monitoring and Control in Aquaculture," *World Aquaculture* 26, No. 2, pages 35–37, 1995; and Chiron et al, "Automated Sample Preparation for Monitoring Groundwater Pollution by Carbamate Insecticides and Their Transformation Products," *Journal of AOAC International* 78, No. 6, pages 1346–1352, 1995.

Known automated ground water monitoring methods passively record measurements in a stagnant well bore and so do not take into consideration the advantages resulting from purging a well prior to recording a measurement. The deleterious effects of this oversight are noted in "Manual of Ground-Water Quality Sampling Procedures," National Water Well Association, 1981, by Scalf et al. This article discloses that the composition of water in and proximate to a well is likely not representative of the groundwater generally in the area. The article "Field Evaluation of Well Flushing Procedures," American Petroleum Institute, 1985, by Gillham et al, discloses that water standing in a polyvinylchloride (PVC) well for as short a period of time as three weeks has demonstrated changes in inorganic chemistry sufficient to cause this water to significantly deviate in quality from groundwater in surrounding locations.

The chemical changes that take place in stagnant borehole water over time are expounded upon in the article "Ground-Water Sampling," in *Practical Handbook of Ground-Water Monitoring,* 1991, by Herzog et al. In Herzog, it is disclosed that temperature, pH, oxidation reduction potentials, and dissolved solids content of stagnant borehole water are adversely affected by influences such as rust and scale on well construction materials, bacteria activity in the well, interactions that take place with the atmosphere, volatilization of organic compounds therein, and effervescence of dissolved gasses in the water over an extended period of time.

In view of these chemical changes, it is generally agreed that a well should be purged of contaminated water prior to the taking of a water quality measurement therein. The exact method for optimally purging a well, however, is still the subject of debate. See Robin et al, "Field Evaluation of Well Purging Procedures," *Ground Water Monitoring Review*, Fall 1987, pages 85–93. Known automated methods fail to even address these purging concerns, consequently, their measurements are often inaccurate.

Known automated methods also have various physical limitations. In the above-mentioned article by Evans, it is pointed out that the size of the pressure transducers and other probes used by known automated water quality monitoring methods limits the minimum diameter of the wells in which they are installed. For at least the foregoing reasons, known automated systems have proven to be less than optimal for monitoring water quality.

Other systems and methods have been developed for sampling water from a well. U.S. Pat. No. 5,224,389 to Jensen, for example, discloses a method of obtaining a sample of groundwater from a well. In the Jensen method, water is pumped from a well until a predetermined criterion (e.g., a minimum variation in electrical conductivity) is satisfied, at which time a sample of what is considered to be substantially non-contaminated water is taken from additional water pumped from the well. The sample is then removed from the well site so that it may be analyzed to determined the quality of water therein.

Jensen is basically a manual system. For example, to implement the Jensen system, a field technician is required to move a mobile sampling unit to the site, and then to turn on the system to initiate purging and sampling. The technician must then remove the unit from the site and take the sample collected therein to a laboratory for testing. The substantial human involvement required to employ the Jensen approach thus makes Jensen as deficient as the conventional systems discussed above.

U.S. Pat. No. 5,553,492 to Barrett discloses taking periodic water level measurements at a plurality of wells, and then transmitting these measurements to a remote location for processing. The Barrett system, however, fails to take a water quality measurement of any kind. Rather, Barrett merely discloses taking water level measurements for the sole purpose of determining the direction of groundwater flow within a region of interest. Furthermore, Barrett requires at least some degree of human intervention to carry out its objectives. For example, water level measurements taken at a well site are transmitted only upon receipt of a user-initiated request.

U.S. Pat. No. 4,717,473 to Burge discloses a self-contained groundwater sampler which automatically collects a water sample from a well at a programmed time. It is also disclosed that the Burge sampler may be adapted to include a unit for analyzing the chemical or physical make up of a collected sample. The Burge system, however, has a number of drawbacks. First, no purging operation is performed prior to analysis. Thus, measurements obtained by the Burge system will likely be inaccurate for reasons previously noted. Second, the Burge system is limited in that it can collect only one sample at a time, and thus requires servicing before obtaining additional samples.

U.S. Pat. No. 5,259,450 to Fischer discloses a pumping apparatus containing a vented packer for minimizing the amount of water to be purged from a well prior to obtaining a sample therefrom. In order to activate the pump, however, a field technician must install a removably mountable controller at the well site, and then must be deployed to retrieve collected samples.

U.S. Pat. No. 5,490,561 to Cardoso-Neto discloses purging a predetermined quantity of water from a well, collecting a sample, and then returning the purged and sampled water to the well. None of these steps, however, is disclosed as being automated, and so a technician must visit this site as well.

From the foregoing discussion, it is evident that while automated systems and methods have been developed for monitoring the quality of water at a sampling site, such systems and methods still require a substantial degree of human intervention and thus are inherently costly and inefficient. Further, known systems and methods fail to take precautions necessary to prevent collected water samples from being contaminated, and thus measurements derived therefrom are likely to be inaccurate.

A need therefore exists for an automated system and method which monitors the quality of water at a sampling site at regular intervals without human intervention, and which does so in a manner to ensure that the samples being tested are free from contamination, thereby enabling a true and accurate determination of water quality to be made.

SUMMARY OF THE INVENTION

The present invention is a system for and method of monitoring the quality of water at a sampling site, without human intervention, by employing a stand-alone control unit at the sampling site which collects water quality measurements in accordance with a computer program. If desired, the invention can be adapted to receive external instructions for deviating from the computer program. The invention thus achieves all the advantages of conventional methods without having their disadvantages.

In particular, the present invention monitors water quality in accordance with the strict sampling protocols observed by manual methods, without requiring the labor and materials costs attendant to manual methods. The present invention observes these protocols, and simultaneously, obtains water quality measurements with a frequency substantially greater than is practically attainable by manual methods.

Further, the present invention outperforms conventional automated methods by automatically transmitting water quality measurements to the base station for analysis, thereby alleviating the need for a field technician to visit the sampling site to collect these measurements. The water quality measurements are transmitted to the base station over a communications network, allowing water quality monitoring to take place on a real-time basis. In one aspect, the present invention may be remotely controlled to monitor the quality of water at a sampling site, by receiving transmissions from a base station over a communications network.

The present invention also purges a sampling site of stagnant or otherwise contaminated water before automatically obtaining a water quality measurement therein. Purging is performed at the site until at least one preselected purge criterion is satisfied, to thereby ensure that the water sample being tested is an accurate representation of water in the well.

The present invention thus provides a method of monitoring quality of water at a sampling site which, in a first embodiment, includes: automatically purging water at the sampling site until at least one preselected purge criterion is satisfied; automatically obtaining a measurement of at least one water quality attribute at the sampling site; and determining the quality of water at the sampling site based on the measurement. The sampling site may include one or more of a well, a group of wells, a multi-level sampler, and a sampling port containing groundwater whose quality is to be monitored.

The purging step of the method of the present invention is preferably automatically performed in accordance with a criterion which corresponds to a minimum number of well volumes or to stabilization of water quality measurements, taken during the purging step, to within a predetermined range. If desired, a plurality of criteria may be used to control the purging step.

The water quality attribute being measured may be a water quality property such as water temperature, specific conductance, pH, or turbidity, a water quality constituent such as dissolved oxygen, dissolved ammonium, or dissolved nitrogen, or water level. Preferably, a combination of these attributes is simultaneously measured to provide a broader statistical basis from which water quality at the sampling site can be determined.

Advantageously, the purging step and the measuring step of the present invention are performed without human intervention, through the implementation of a computer program which defines the time, manner, and extent to which water quality measurements are to be taken at the sampling site. The computer program may define, for example, performance of the purging and measurement obtaining steps in accordance with a predetermined time schedule, or at times when changes in water quality at the sampling site are expected to occur.

If desired, the computer program may be preempted in order to receive instructions from an external source (e.g., an on-site field technician or a remote base station) to cause water quality measurements to be taken in a manner or at a time which deviates from the computer program. For example, upon detection of a trend or an abrupt change in water quality measurements, the control program may be preempted to allow the taking of water quality measurements with a frequency greater than that programmed. Thus, the present invention is highly versatile, in that it can be programmed and also externally modified to monitor water quality under virtually any conditions, whether anticipated or unexpected, and with any desired measuring frequency.

Other aspects of the present invention include automatically obtaining a plurality of intermediate measurements of at least one water quality attribute during the purging step, and selecting the measurement representing water quality at the site to be that intermediate measurement existing at a time when the preselected purge criterion, or criteria, is satisfied.

Another aspect of the present invention includes automatically storing water quality measurements in a memory, which measurements may then be downloaded by a field technician at the sampling site or transmitted to a remote base station over a communication network, such as a land-based telephone line or a wireless communications link. Communication to the base station may be initiated upon request or automatically in accordance with a computer program controlling the steps of the method. A computer program in the base station may also control such communication. The communications network may also be used to transmit instructions to the sampling site to preempt the computer program.

Another aspect of the present invention includes monitoring the condition of the sampling site, and automatically terminating the method upon detection of an error condition. Signals may then be automatically transmitted to a base station along the communications network to alert technicians of the error condition.

Another aspect of the present invention includes automatically obtaining a plurality of measurements of at least one water quality attribute over a predetermined interval of time, and determining the degree to which water quality at the sampling site has changed over the predetermined interval based on the plurality of measurements. The manner of execution of these steps may be defined by the computer program controlling the method, and advantageously each of the plurality of measurements may be preceded by completion of a purging step, as defined above. The measurements may then be automatically stored in memory to create, therein or elsewhere, an historical record of water quality measurement values over a time interval of interest.

Also, in accordance with the present invention, the quality of water may be monitored at a plurality of sampling sites within an area of interest by obtaining water quality measurements at the sampling sites in accordance with steps which include: automatically purging water at each sampling site until a preselected criterion is satisfied, and automatically obtaining a measurement of at least one water quality attribute at each sampling site. As in the first embodiment, the steps taken at each site are performed under control of a computer program. Water quality attribute measurements for all sites are then collected at a base station, and the quality of water in the area of interest is determined based on these collected measurements.

A first embodiment of a system for performing the method of the present invention of monitoring quality of water at a sampling site includes a pump for purging water from the sampling site; a probe contacting water at the sampling site; and a control unit which, in accordance with a computer program, controls the pump to purge water from the sampling site until at least one preselected purge criterion is satisfied, and controls the probe to take a measurement of at least one water quality attribute to provide an indication of water quality at the sampling site. Preferably, the control unit is a stand-alone device which autonomously controls operation of the pump and probe in accordance with the computer program.

The system further includes a memory unit for storing water quality measurements taken by the probe, and a communications port on the control unit for downloading measurements in the memory unit by a field technician. In addition, the control unit may be equipped with a transceiver for transmitting measurements stored in memory to a base station along a communications network. Further, the control unit may be adapted to receive signals from an external source (e.g., an on-site technician or a base station) to activate the system and/or to cause the control unit to control the pump and probe in a manner which deviates from the computer program.

The process further includes diagnostic logic for monitoring the status of the sampling site based on signals received from sensors disposed at predetermined locations throughout the sampling site. In operation, the diagnostic logic causes the control unit to deactivate the pump and probe when the sensor signals indicate that an error condition exists in the system.

In a second embodiment of the system of the present invention, water quality attribute measurements taken at a plurality of sampling sites within an area of interest are transmitted to a base station to create an historical record of such measurements, and water quality for the entire area of interest is then determined based on these measurements. A communications network is included for conveying the measurements taken at the sampling sites to the base station.

BRIEF DESCRIPTION OF THE DRAWINGS

These and other aspects and advantages of the present invention are more apparent from the following detailed description and claims, particularly when considered in conjunction with the accompanying drawings, in which:

FIG. 1 is a schematic diagram showing a first arrangement of the present invention as implemented to monitor water quality at a sampling site;

FIG. 2 is a schematic diagram showing a second arrangements of the present invention as implemented to monitor water quality at a sampling site;

FIGS. 9A–9G are graphs comparing measurements of various parameters obtained in the first working example of the present invention with measurements manually taken and those taken in a laboratory;

FIG. 10 is a table setting forth the results of a chemical analysis of samples manually taken during sewage treatment plant decommissioning;

FIGS. 11A–11E are graphs showing purge values in a second working example of the present invention;

FIGS. 14A–14E are graphs showing water property and constituent measurements taken in the third working example of the present invention.

DESCRIPTION OF PREFERRED EMBODIMENTS

Figure 3A:
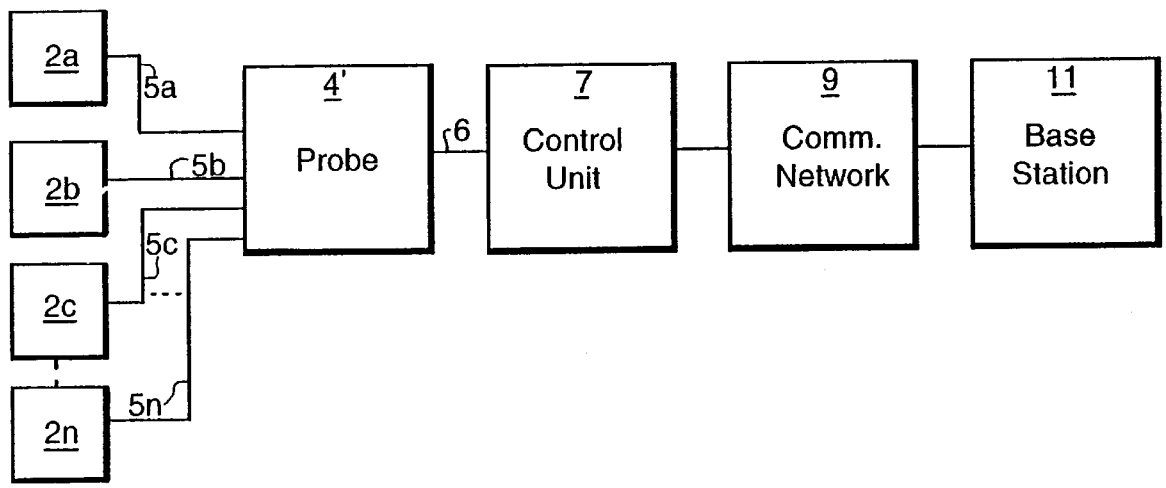
FIG. 3A–3C are schematic diagrams showing alternative arrangement of the present invention as implemented to monitor water quality at a plurality of sampling sites.

The present invention monitors the quality of water at a ground water sampling site. For example, as shown in FIG. 1, the sampling site 1 may include a well 2 filled with water to a level indicated by reference numeral 3. A probe 4 for measuring water level and one or more water quality attributes is submerged in the well, along with a pump 5 for pumping water therefrom. Signal line 6 carries signals from probe 4 to a control unit 7 located at the surface of the sampling site. In an alternative arrangement, depicted in FIG. 2, water quality probes 4' can be housed in a flow-through chamber at or near the ground surface. In either case, the pump output can go to an appropriate site, such as a waste water location. Control unit 7 contains a processor for executing a computer program defining the steps of the method according to the present invention. Control unit 7 may be adapted to allow the computer program to be preempted, either manually by a technician at the site or automatically based on control signals transmitted from a base station 11 via a communication network 9, to thereby cause water quality to be monitored in a manner which deviates from the computer program. Preempting in this manner may be temporary or permanent.

Figure 3B:
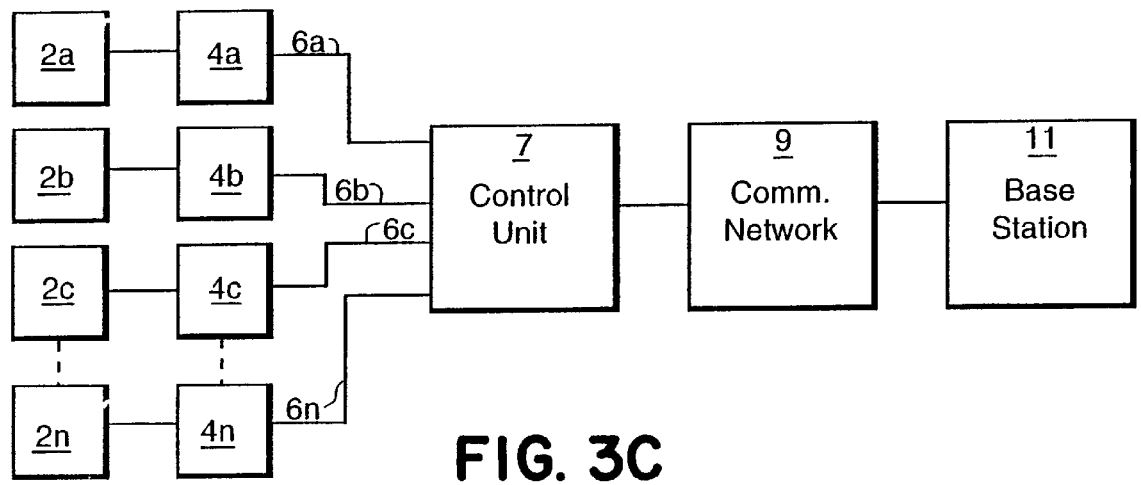
Figure 3C:
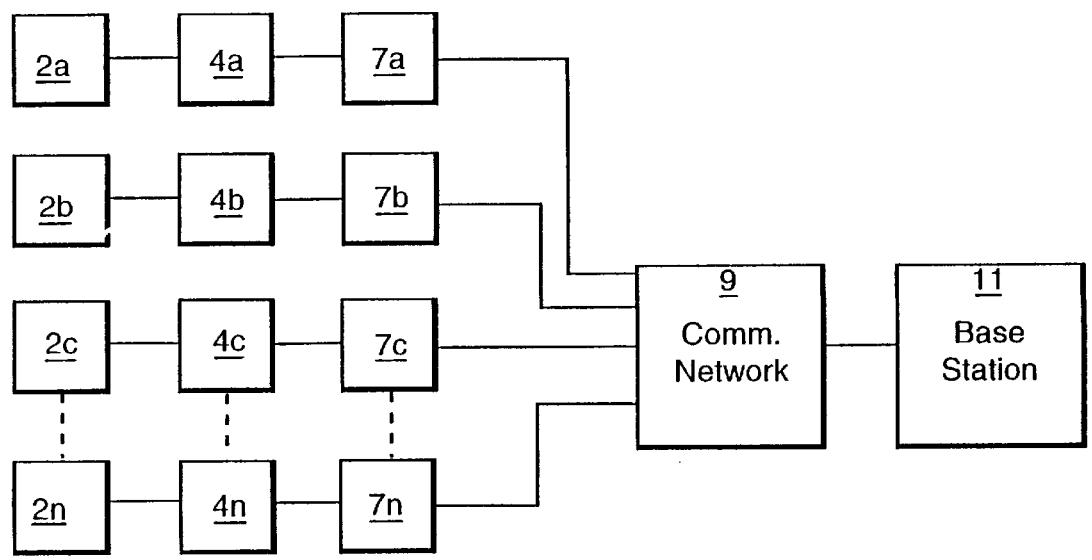

Further, while the present invention may advantageously operate in accordance with a sampling site as shown in FIGS. 1 and 2, it need not be so limited. Rather, advantageously, the method of the present invention may be adapted to monitor water quality in a manner specifically tailored to any site configuration, simply by making commensurate changes to the computer program and/or the hardware used to implement the steps defined therein. Thus, FIGS. 3A, 3B, and 3C depict arrangements for multiple wells or samplers. In FIG. 3A water from a plurality of closely spaced wells 2a, 2b, 2c, . . . 2n is carried by water lines 5a, 5b, 5c, . . . 5n to a water quality probe 4' which is then coupled by signal line 6 to control unit 7 and the rest of the system. FIG. 3B depicts an arrangement in which a water quality probe 4a, 4b, 4c, . . . 4n is provided at each well 2a, 2b, 2c, . . . 2n and is coupled by a respective signal line 6a, 6b, 6c, . . . 6n to control unit 7 and the rest of the system. FIG. 3c depicts an arrangement in which a control unit 7a, 7b, 7c, . . . 7n is also provided at each well 2a, 2b, 2c, . . . 2n.

Control unit 7 can be a commercially available data logger capable of receiving measurement signals via line 6 from probe 4 or 4', storing those measurement signals in a memory, and transmitting the measurement signals in a memory, and transmitting the measurement signal, either in real time or from storage, to communication network 9. In addition, control unit 7 receives control signals generated at base station 11 and transmitted via communication network 9 to control the operation of the equipment at the sampling site. All of the equipment at the sampling site, including pump 5, probe 4 and control unit 7, may be powered by conventional methods, including battery power and solar power. Further, if desired, pump 5 may be powered by a compressed gas, such as nitrogen.

With the foregoing considerations in mind, the method of the present invention commences with purging of the well to eliminate stagnant water or water which has become contaminated by one or more natural and/or artificial influences. Elimination of this water is accomplished by pumping water from the well until at least one preselected purge criterion is satisfied, at which time it is concluded that the water then in the well is sufficiently purged so as to allow an accurate water quality measurement to be taken.

The first step in accomplishing the purge is determining the amount of water to be purged. This can be done by estimating an appropriate amount or by measurement and calculation. If the purge volume is estimated, historical ground-water levels may be used to determine the required purge volume. If the purge volume is to be calculated from measured values, the water level is measured and recorded before the purge cycle, and the control system 7 calculates the required purge volume based upon the amount of water in the well.

The purge criterion used to govern the purging step may advantageously be selected to optimally match the chemical constituents, sampling installations, and hydrogeologic features particular to each well. The purge criterion can also be modified to reflect chemical and hydrogeologic changes that take place in the well over time.

The purge criterion, or criteria, governing the purging step of the present invention may include evacuation of a predetermined volume of water from the well, and stabilization of one or more water quality attributes taken during successive measurements during the purging step. Optionally, the purging step may be performed until a plurality of such purge criteria are satisfied. The water that has been purged from the well is expelled away from the well in order to prevent unpurged water in the well from being contaminated.

A second step of the method of the present invention involves automatically obtaining a measurement of at least one water quality attribute, for example, via probe 4 or 4'. The attribute measured may be a water quality property such as water temperature, specific conductance, pH, or turbidity, or a water quality constituent such as dissolved oxygen, dissolved ammonium, or dissolved nitrogen. Preferably, a plurality of these attributes are measured to provide an enhanced indication of water quality in the well.

A third step of the method of the present invention involves determining the quality of water in the well by analyzing the one or more water quality attributes that have been measured. This step may be performed manually by a skilled technician or automatically by a computer, or both. At least some type of processing of these measurements is preferably performed on site in accordance with the computer program controlling the method.

The method of the present invention may include a number of additional steps. For example, one or more of the water quality attribute measurements taken during the measuring step may be automatically stored in a memory within control unit 7. These measurements may then be transmitted to a remote base station 11, either automatically or upon request by the base station, and/or may be downloaded from the memory upon request to a field technician at the sampling site. Preferably, the memory may be used to create an historical record of water quality attribute measurements, which record can then be analyzed to provide an indication of how water quality has changed at the sampling site over time. Optionally, water quality attribute measurements stored in the memory may be automatically transmitted at regular intervals to the base station 11, where they are compiled into an historical record for subsequent evaluation. Further, the water quality measurements may be communicated from the sampling site to base station 11 via communications network 9 to permit water quality monitoring to be determined on a real-time basis. Network 9 may be a land-based telephone line or a wireless communication link such as a cellular telephone link, an RF link, and a satellite link, any combination thereof, or any other communication method.

Further, network 9 may be bidirectional in nature to permit a technician at the base station 11 to communicate instructions to control unit 7, for example, to access measurement data therefrom and/or to preempt the computer program driving control unit 7 to effect temporary or permanent changes in water quality monitoring at the site, e.g., to effect a change in sampling frequency.

As previously noted, the time, manner, and extent to which water quality measurements are taken at the sampling site may be defined by the computer program in control unit 7. This program may be written to control the pump and probes to record a plurality of measurements of one or more water quality attributes in accordance with a predetermined schedule, with each measurement or set of measurements being preceded by a purging step. The predetermined schedule may be defined, for example, to cause the taking of measurements at regular intervals of a number of hours, days, or weeks, taking into consideration factors such as local groundwater velocities and the time scale of various chemical and transport processes of interest.

The computer program may also control the automatic taking of water quality measurements at times when changes in water quality are expected to occur, upon the occurrence of a predetermined condition, or upon the detection of a trend in water quality attribute measurements. Also, technicians at base station 11 may transmit instructions to control unit 7 to facilitate the taking of water quality measurements upon detection of a trend or an abrupt change in water quality measurements. One skilled in the art, therefore, can appreciate that, by making appropriate modifications to the computer program in control unit 7, the method of the present invention can monitor water quality at a sampling site in virtually any desired manner.

In accordance with another aspect of the present invention, the control program may be preempted to permit a field technician to take manual measurements of one or more water quality attributes at the site. These manual measurements may then be used to verify accuracy of measurements automatically taken in accordance with the method of the present invention.

In another aspect of the method of the present invention, the status of the sampling site may be monitored based on instrumentation and equipment signals indicating, for example, the existence of an error condition. These conditions may include, for example, low water level, insufficient power supply, malfunctioning equipment at the site, and an indication that at least one water quality attribute obtained during the measuring step lies outside a predetermined range. Once an error condition has been detected, a warning signal may be automatically transmitted to the base station 11 or may be downloaded at the site to alert a field technician of the need for maintenance, repair, or recalibration. Upon detection of such error data, the purging and measuring steps of the present invention may be manually or automatically performed to determine an updated status of the sampling site.

Figure 4:
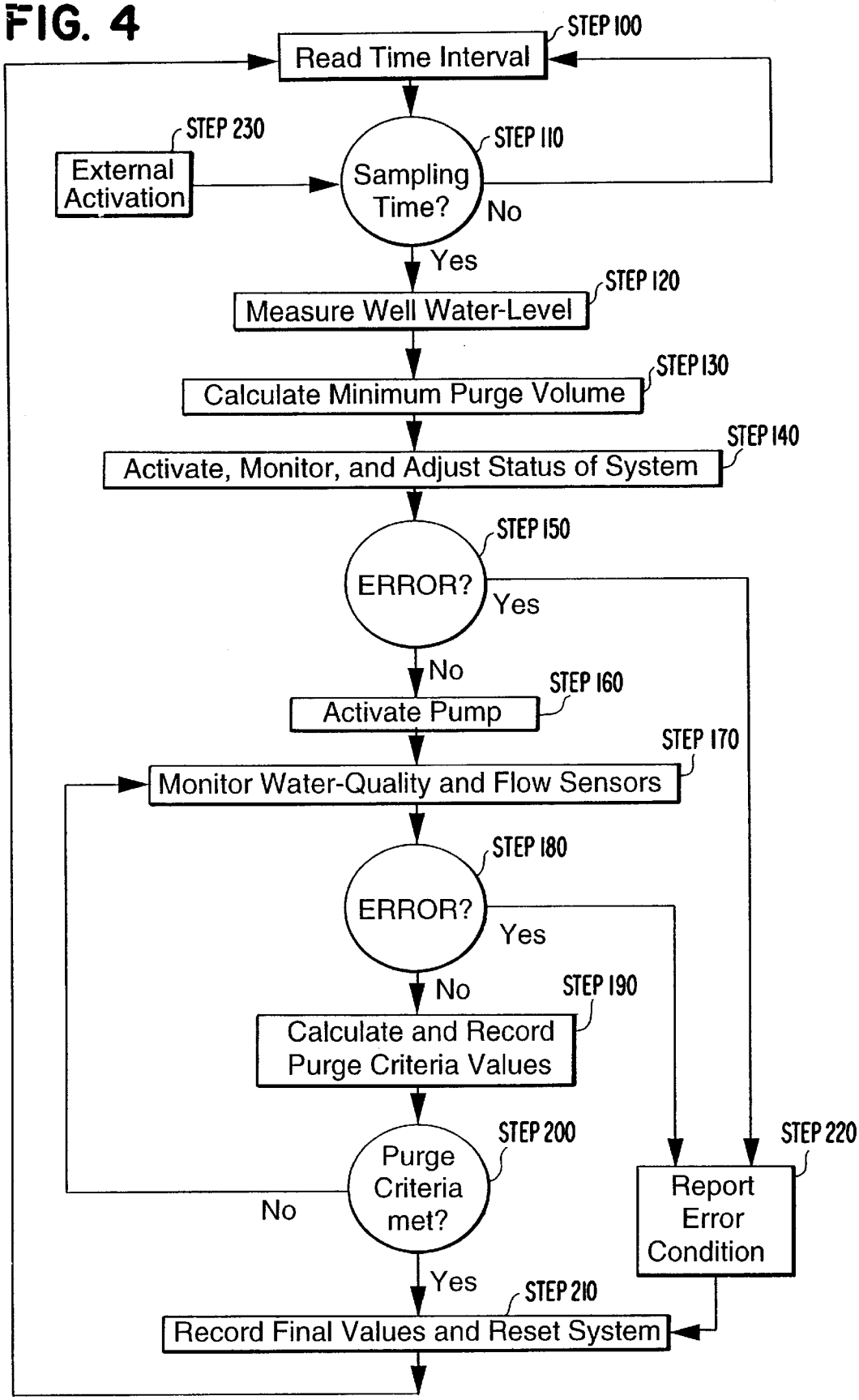
FIG. 4 is a flow chart of a preferred embodiment of a method of the present invention.

FIG. 4 is a flow chart of steps included in the method of the present invention. At step 100, an internal clock value is determined and, at step 110, this value is compared with a time schedule to determine whether the value corresponds to a sampling time. If not, comparisons continue between internal clock values and the programmed time schedule until a match occurs. Then, a process is initiated wherein a well water level measurement is taken (step 120), a minimum purge volume is calculated based on the water level measurement (step 130), and a status check is performed (step 140).

More specifically, in step 140, a series of self tests is initiated to monitor the status of the site. In step 150, if an error is detected during the status check, existence of the error is recorded and reported, along with the corresponding sampling time (step 220), status values are recorded, and the system is reset and returned to step 100. The error condition may be reported either by storing warning data in memory, and/or by automatically transmitting a warning signal to a base station to alert a field technician so that repair can be made.

If no error is detected in step 150, the control unit activates a pump (step 160) to purge the well by an amount of water commensurate with the calculated minimum purge volume calculated in step 130. In step 170, the control unit activates the probe 4 in the well during the purging process to measure and record in memory preselected water quality properties and constituents until the purge criteria are met.

In step 180, another series of self tests is initiated to monitor the status of the site during purging. If an error is detected, the purging and measuring steps are terminated, the error is recorded and reported to alert a field technician (step 220), the status values in existence at the time are recorded, and the system is returned to step 100. If no error is detected, purging continues, during which time the probe is activated to calculate and record purge criteria values (step 190).

In step 200, a determination is made as to whether the calculated and recorded purge criteria values have satisfied the preselected purge criteria. If not, steps 170, 180, 190, and 200 are repeated until either an error is detected and steps 220 and 210 are performed or a determination is made that the purge criteria have been satisfied. When the purge criteria have been satisfied, representative water quality property and constituent measurements are recorded in memory as final values, and if desired are transmitted to the base station 11. The control unit then returns to step 100 and monitors the internal system clock until it is time to once again initiate the process.

FIRST WORKING EXAMPLE

Figure 5:
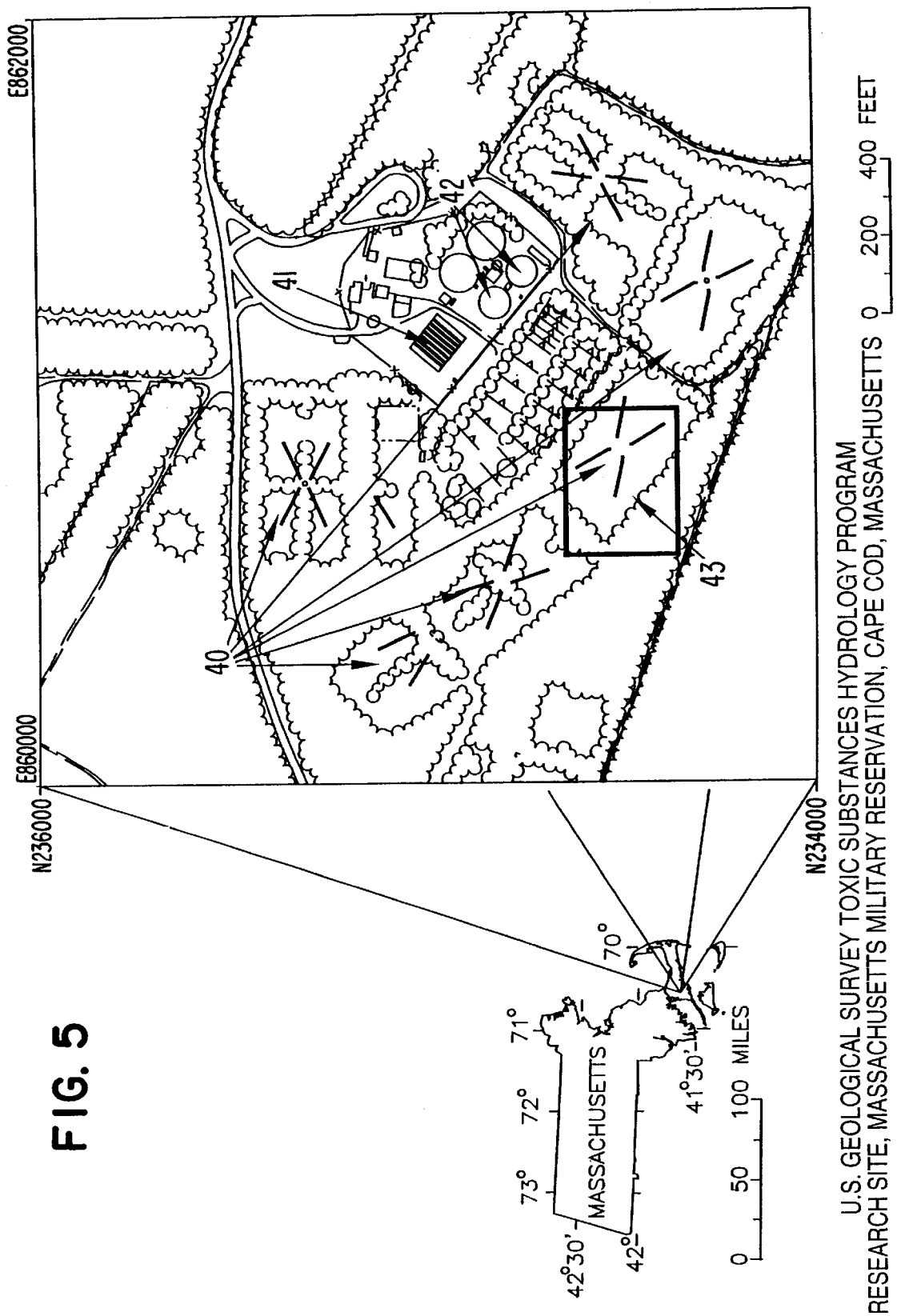
FIG. 5 is a diagram of a sampling site where the working examples of the present invention were carried out.

FIG. 5 is a diagram of an area where a first example of the of the present invention was employed at the U.S. Geological Survey (USGS) Toxic Substances Hydrology Program Research Site on the Massachusetts Military Reservation in Cape Cod, Mass. As shown FIG. 5, the site included a plurality of sand infiltration beds 40 for disposing of sewage effluent from a nearby sewage treatment plant containing an Imhoff tank 41 and a plurality of clarifiers 42. Two wells were drilled into the infiltration beds within a region 43 to facilitate the implementation of the present invention.

The Cape Cod site was selected for two reasons. First, pronounced changes in groundwater quality at the site were expected to occur as a result of decommissioning activities taking place at the sewage treatment plant. These decommissioning activities included the introduction of a large pulse (e.g., 2 to 3 million gallons) of partially treated sewage effluent into the infiltration beds, followed by a large pulse (e.g. 1.4 million gallons) of sewage effluent caused by chemical treatment of plant tanks, followed by a period of cessation of sewage effluent discharge. This was expected to cause geochemical changes in ground water at the site over a long period of time as recharge from precipitation flushed constituents from site soils and sediments. The Cape Cod site therefore offered a prime opportunity to test performance of the system and method of the present invention against conventional manual sampling methods.

Second, the site contained unconsolidated deposits of sand and gravel, which together formed a permeable unconfined aquifer (water table) proven to be particularly well suited for a short-term ground water quality investigation.

Figure 6:
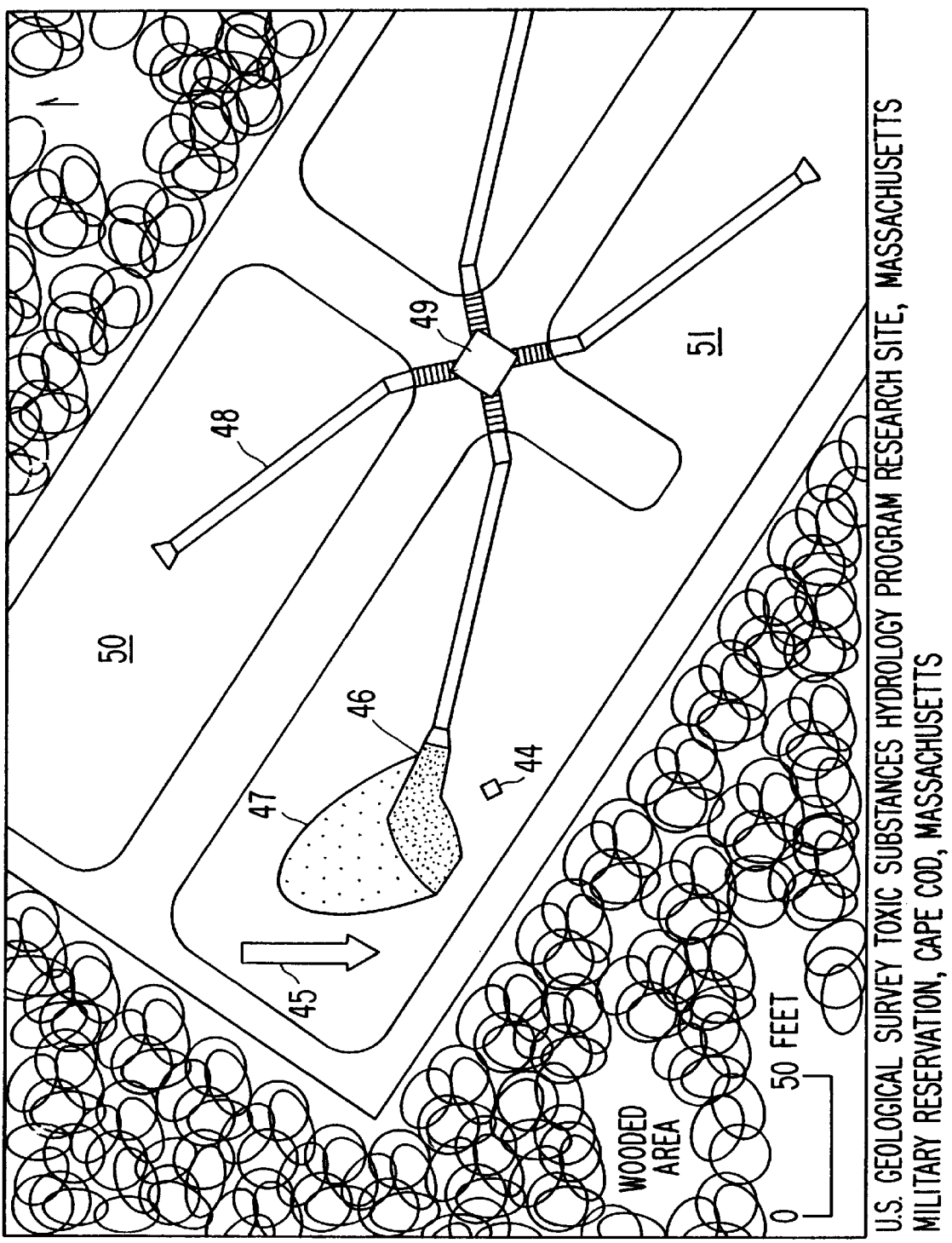
FIG. 6 is a diagram showing an enlarged view of the sampling site shown in FIG. 6.

FIG. 6 is a diagram showing an enlarged view of the region 43 of FIG. 5. At this region, two wells and a shelter for housing electronics, instrumentation, equipment, and other hardware for the system were emplaced in an infiltration bed 44 approximately 20 feet down gradient of a pond area 46 constructed to form a line source of infiltrating water. An arrow 45 indicates the general direction in which ground water flowed in the region. Also shown is a semi-elliptical area 47 of the bed behind an impoundment that routinely flooded when flow rates from a discharge pipe 48 exceeded the infiltration capacity of the pond area 46. A sewage distribution box 49 was connected to the discharge pipe. Reference numerals 50 and 51 represent adjoining sand infiltration beds.

Figure 7:
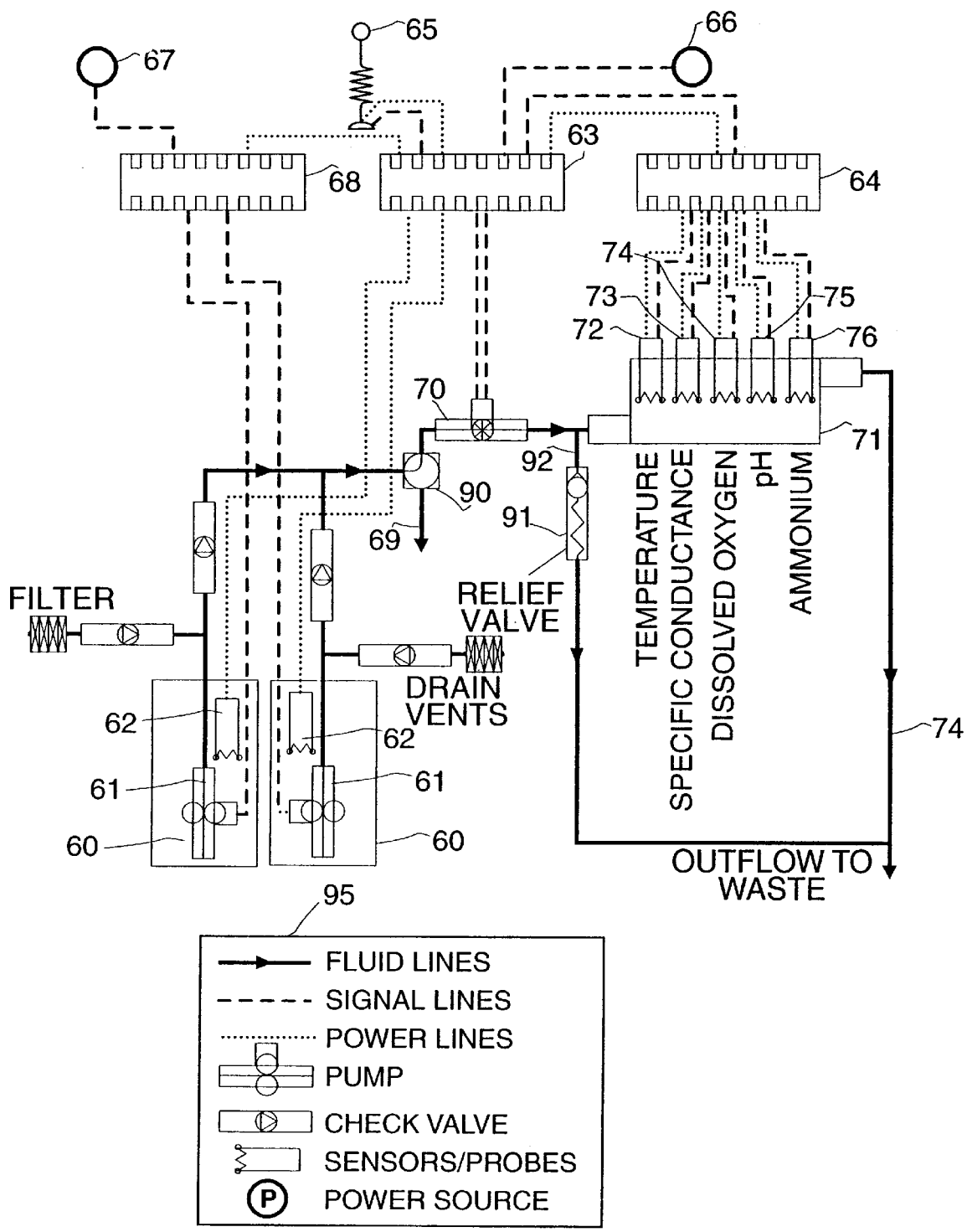
FIG. 7 is a diagram showing a water quality monitoring system in accordance with a first working example of the present invention.

FIG. 7 is a block diagram of the water quality monitoring system. Two 2-inch-diameter polyvinylchloride wells 60 were emplaced at infiltration bed 44 for monitoring ground water quality. One of the wells was screened from about 5 feet above to about 5 feet below the water table, determined to be approximately 24 feet below the land surface. The other well was screened from about 5 to 10 feet below the water table. Each well was equipped with a QED bladder pump 61 for conducting a purging operation and a Keller 0–2.5 psi pressure transducer 62 for measuring the water level.

As also shown in FIG. 7, the system included a control unit 63 having an integral memory and connected to an additional memory (not shown) for storing water quality property and constituent measurements as measured by sensors 62 and 72–76. The control unit 63 was a Campbell Scientific Incorporated CR10 data logger programmed to monitor the quality of water in accordance with the present invention. The additional memory was a CSI SM192 solid state storage device.

Because electric power and telephone lines were not readily available at the site, batteries recharged by solar panels 66 were used to power the control unit, memory, and other electronics, and a nitrogen gas source 67 was used to power the pumps through a pneumatic logic controller 68. It is noted, however, that a battery/solar panel arrangement similar to that used for powering the system electronics could also have been used to power the pumping equipment. A CSI DC112 cellular phone modem 65 was used to establish communications between the control unit and a base station.

As further shown in FIG. 7, a Plastomatic hand-operated three-way valve 90 was placed near the beginning of the flow train to divert the flow of water from the wells to enable a manual sample to be collected through a sampling port 69. A ½-inch flow sensor 70, by Data Industrial, monitored the flow rate of water pumped through the system during purging and recording periods.

A Hydrolab Multiprobe containing sensors 72–76 was used to measure respective values of temperature, specific conductance, dissolved oxygen content, pH, and ammonium in samples of well water diverted into a flow cell 71. Operation of the multiprobe was controlled by control unit 63 via sensor controller 64. Other probes (not shown) were provided to monitor nitrogen pressure, shelter air temperature, battery voltage, and other parameters. Fluid line 92, via relief valve 91, and fluid line 74 provided ways of egress from the system. A legend 95 is provided to indicate the manner of connection of features in the system.

Figure 8A:
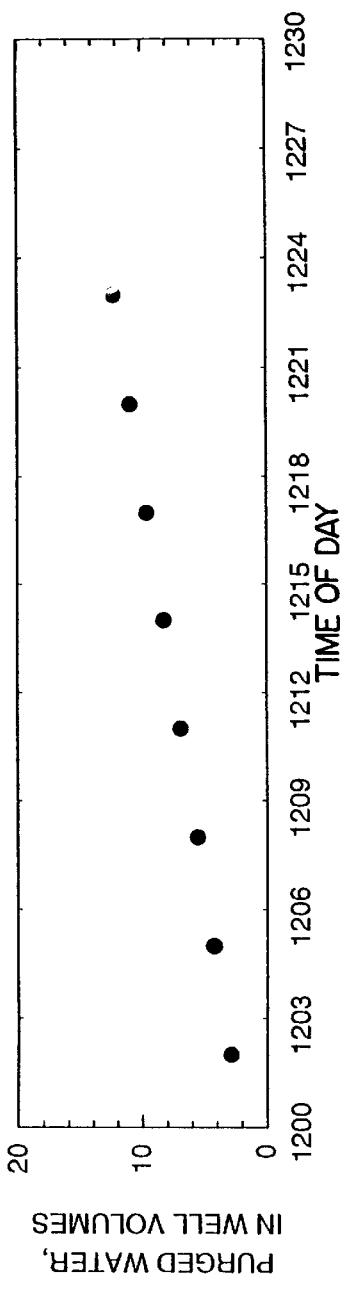
FIGS. 8A–8F are graphs showing purge values in the first working example of the present invention.
Figure 8B:
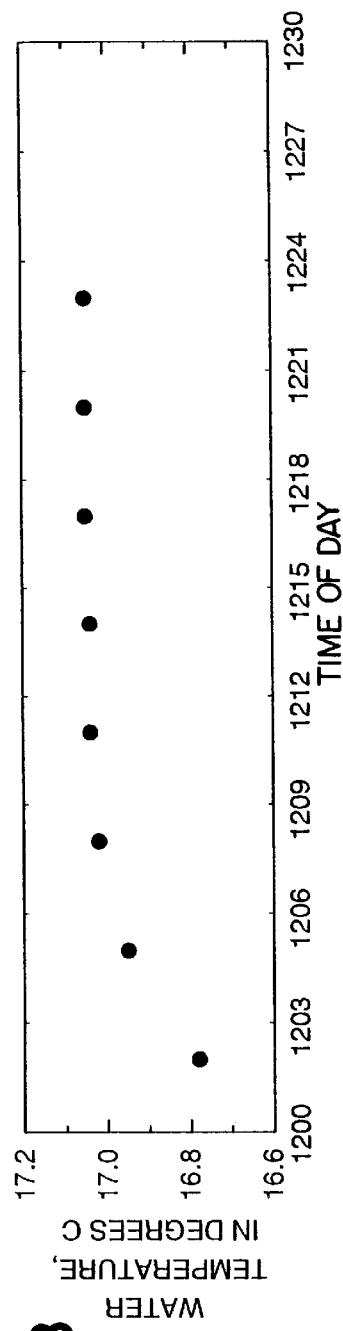
Figure 8C:
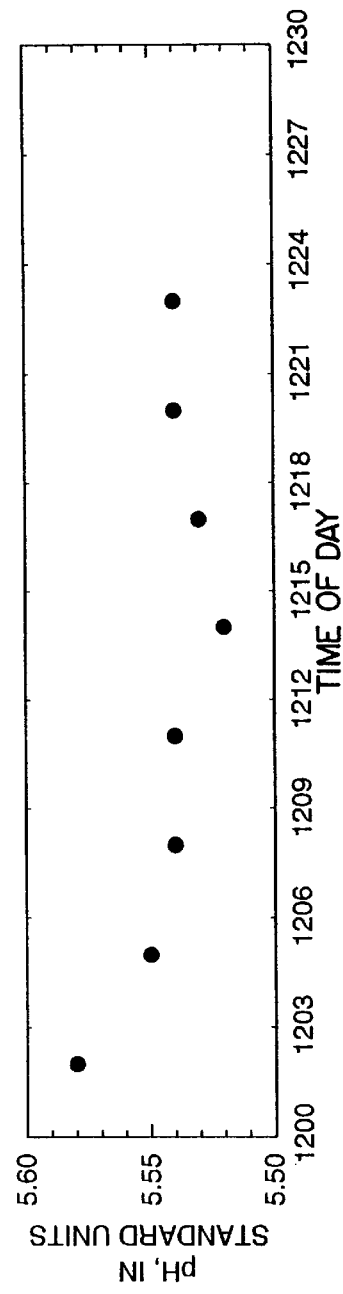
Figure 8D:
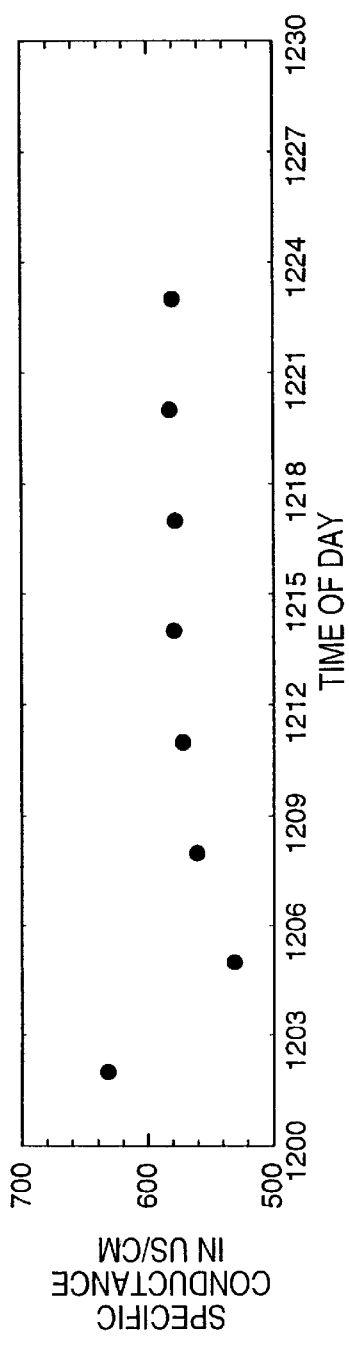
Figure 8E:
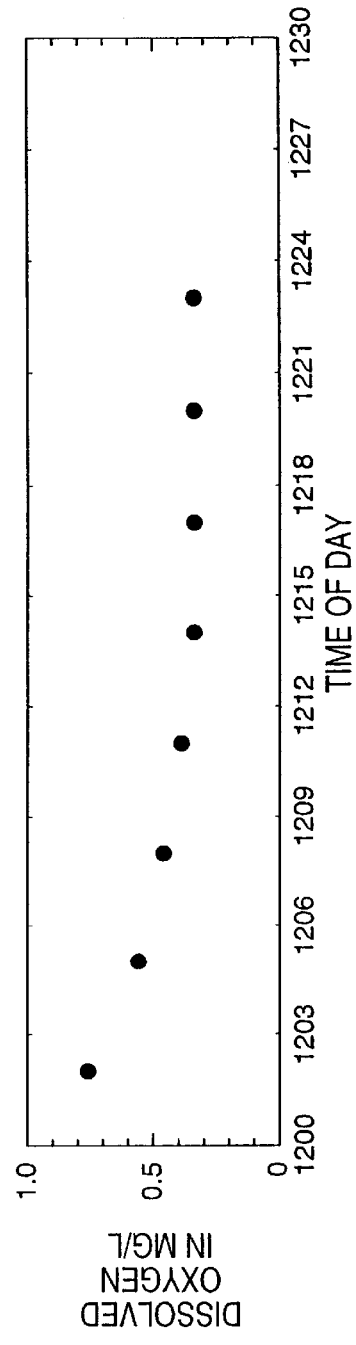
Figure 8F:
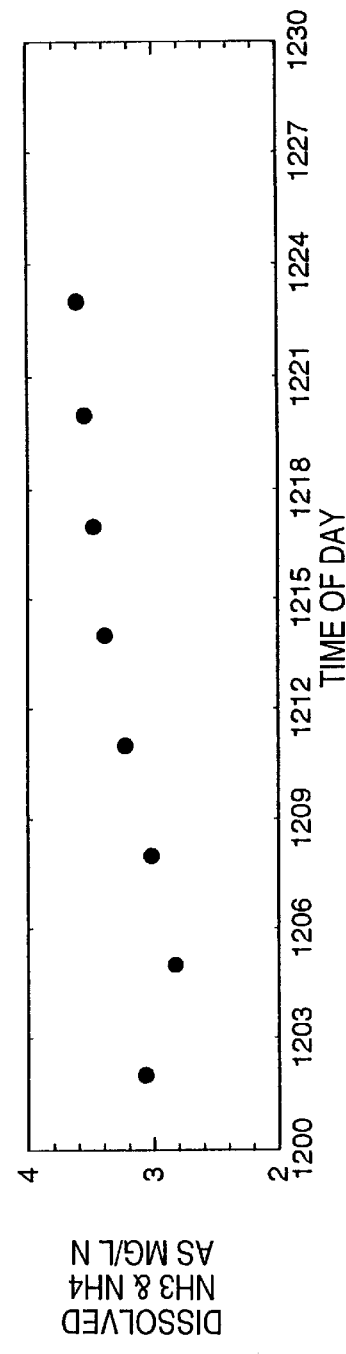

In operation, the system purged water from the wells until a purge criteria based on geochemical stability was satisfied. Prior to purging, well water level was measured by probe 62 and the volume of water in the well was then calculated. Purging then began, and a flowmeter 70 monitored the pump rate during purging and sampling. As shown in FIGS. 8A–8E, purge values were recorded at regular intervals. FIG. 8A is a graph showing the purge volume values during purging. FIG. 8B is a graph showing water temperature values during purging, FIG. 8C is a graph showing values of pH during purging, FIG. 8D is a graph showing specific conductance values during purging, and FIG. 8E is a graph showing values of dissolved oxygen during purging. FIG. 8F is a graph showing dissolved ammonia as mg/L nitrogen. In accordance with a predetermined protocol, the medians of the last five measurements of selected properties and constituents were recorded as the final values representing the quality of groundwater at the wells.

During testing, water quality properties and constituents, as identified in FIG. 9 were measured at times based on expected changes in ground water quality. Typically, a daily time interval was used, except during times of abrupt water quality change when measurements were taken every twelve hours. The data stored in the system memory was either downloaded into field technician's laptop computer at the sampling site or retrieved remotely via a cellular phone modem.

The system operated successfully throughout the period of testing, and sufficient data was collected to demonstrate that the water quality property and constituent measurements obtained were at least equivalent to data obtained by manual sampling methods using the same protocols.

FIG. 10 is a table setting forth the results of chemical analyses of samples taken in accordance with the manual method during the period of plant decommissioning. As shown, measurements of water properties and constituents were taken of samples at the plant during decommissioning and of samples of ground water at the sampling site. At the plant, specific measurements were taken of effluent samples from the clarifier (1), the Imhoff tank (2), and the sludge press (3). At the sampling sites, measurements were taken of ground water existing prior to release of plant effluent (5) and of ground water existing after release of plant effluent (6, 7, 8). FIG. 10 also shows measurements of the following chemical properties of plant and ground water samples: alkalinity, hardness, chloride, bromide, sulfate, fluoride, calcium, magnesium, sodium, potassium, iron, manganese silica, ammonia or ammonium, nitrite nitrogen, nitrate phosphorus, and orthophosphate.

The graphs of FIG. 9 compare measurements obtained by the system with manual measurements taken in the field and in a laboratory. In these graphs, the abscissa corresponds to time measured in increments of days over approximately a six month period, and the ordinate corresponds to scale values for the water properties and constituents measured. Also, in all but FIG. 9A, the graphs show daily measurements taken by the system as dots, weekly measurements taken by the system as crossed points, manual measurements taken in the field as inverted triangles, and manual measurements taken in a laboratory as upright triangles, with some manual field measurements being taken on the same date as manual laboratory measurements.

In implementing the manual technique, samples were collected from the wells using an overflowing aspirated bottle connected to sampling port 69 shown in FIG. 7, and these samples were collected approximately every two weeks. Manual measurements of water temperature, specific conductance, and pH were obtained using laboratory-calibrated field meters, e.g., Orion 290A and Orion 124 meters. Water-quality samples were also sent to the U.S. Geological Survey National Water Quality Laboratory (NWQL) for testing.

Manual measurements of dissolved oxygen greater than 0.9 mg/L were determined by Winkler titrations, and manual measurements of dissolved oxygen less than 1.0 mg/L were determined by a CHEMetrics kit. During the study period, pH remained below 9, therefore almost all ammonia in solution was attributable to ammonium ions. Measurements of dissolved ammonia/ammonium as nitrogen, determined by a CHEMetrics kit, and the NWQL did not differentiate between species. Samples for analysis by the NWQL of dissolved ammonia as nitrogen, and other nitrogen species were also collected about every two weeks as duplicates for field measurements and to quantify nitrogen specification.

Equipment blanks (i.e., samples of deionized water processed through all pumps and wetted parts of the system) were analyzed at NWQL for concentrations of major ions and nutrients. These samples were taken prior to installation of the system to ensure that the system did not contribute measurably to the water quality constituents measured in the samples collected.

Recalibration and maintenance of the probes were performed at frequencies suggested by manufacturers. Water quality property and constituent measurements were remotely retrieved at regular intervals through modem 65 and then examined to determine changes and/or trends in water quality. If a change or trend was detected, field technicians were dispatched to take independent manual measurements to substantiate the findings.

Figure 9C:
Figure 9D:
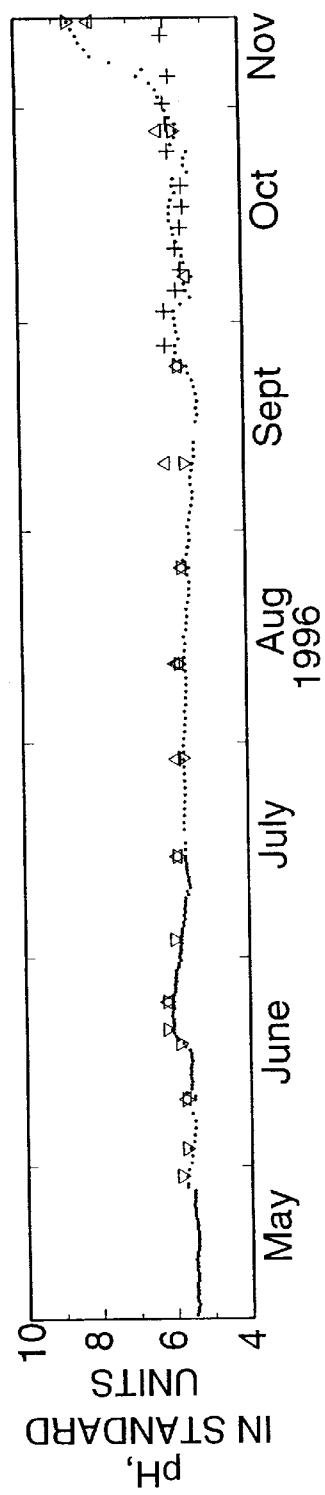

FIG. 9 shows the results obtained by the system against the manual measurements. FIG. 9A is a graph showing the precipitation that occurred throughout the testing period. Lines 111 and 222 show periods of time when the sewage plant was discharging to the infiltration bed at the sampling site. Line 111 indicates a period during which a surge occurred due to a sewage plant discharge, and line 222 indicates a period during which a surge occurred due to a sludge press discharge. FIG. 9B compares water level measurements taken by the system and manual measurements obtained in the field and in a laboratory; FIG. 9C compares specific conductance measurements; FIG. 9D compares pH measurements; FIG. 9E compares water temperature measurements; FIG. 9F compares dissolved oxygen measurements; and FIG. 9G compares dissolved ammonium measurements.

As shown by FIG. 9, the measurements obtained by the system were closely correlated to those obtained by the manual technique for all properties and constituents. Automated pH measurements (FIG. 9D) were slightly but consistently lower than the laboratory and manual field measurements. This discrepancy was attributable to pressurization of the membrane in pH probe 75 caused by elevated water pressure in flow cell 71 (FIG. 7).

The close correlation between the manual field measurements and those obtained by the system was largely attributable to the remote communication capability of the system via modem 65. With this capability, automated measurements could advantageously be examined in real time, at any time, from a home base station. Unexpected changes in water quality prompted a site visit for manual calibration and testing. On one particular occasion, a field visit confirmed that a membrane in ammonium probe 71 had failed when substantial increases in ammonium concentrations occurred in mid July. The erroneous measurements were then removed and a no-data entry was made for that interval, as shown by arrow 113 in FIG. 9G.

The tests performed at the Massachusetts site demonstrated that the present invention was a highly valuable tool for monitoring the quality of water at a sampling site, and moreover provided a number of advantages over manual methods.

Perhaps most notably, the system was able to produce water quality measurements that were substantially equivalent to those obtained by the manual method using identical protocols. See FIG. 9. However, the system achieved this equivalency automatically, i.e., without human intervention, and thus in a substantially less burdensome manner.

More specifically, in order to implement the manual method, technicians were required to visit the sampling site with sensors and equipment in hand, making the manual method cumbersome, time-consuming, and expensive to employ. In contrast, the system of the present invention measured a plurality of water quality attributes remotely, and thus free from the costs and complexities incumbent upon the manual system.

The system was also able to take measurements with a much higher frequency than the manual method. As shown in FIG. 9, automated measurements by the system were taken daily to provide a real-time indication of water quality at the well site. In contrast, because of labor costs and other practical considerations, manual measurements were taken approximately every two weeks. The manual method thus provided a significantly less comprehensive indication of the manner in which water quality changed throughout the testing period.

Advantageously, the system also automatically recorded an array of geochemical and hydrologic properties of groundwater at the sampling site. Discharges of plant effluent and normal to high precipitation levels were not notable in measured water levels because of the high hydraulic conductivities of the aquifer. However, the effect of effluent discharge on the geochemical and hydrologic properties of groundwater at the site proved to be relatively rapid, e.g., about five to six days for specific conductance, about eight to ten days for pH and ammonium, about three days for water temperature, and about one day for dissolved oxygen. Further advantageously, the system proved that it could automatically monitor water quality at more than one well simultaneously.

SECOND WORKING EXAMPLE

Figure 11D:
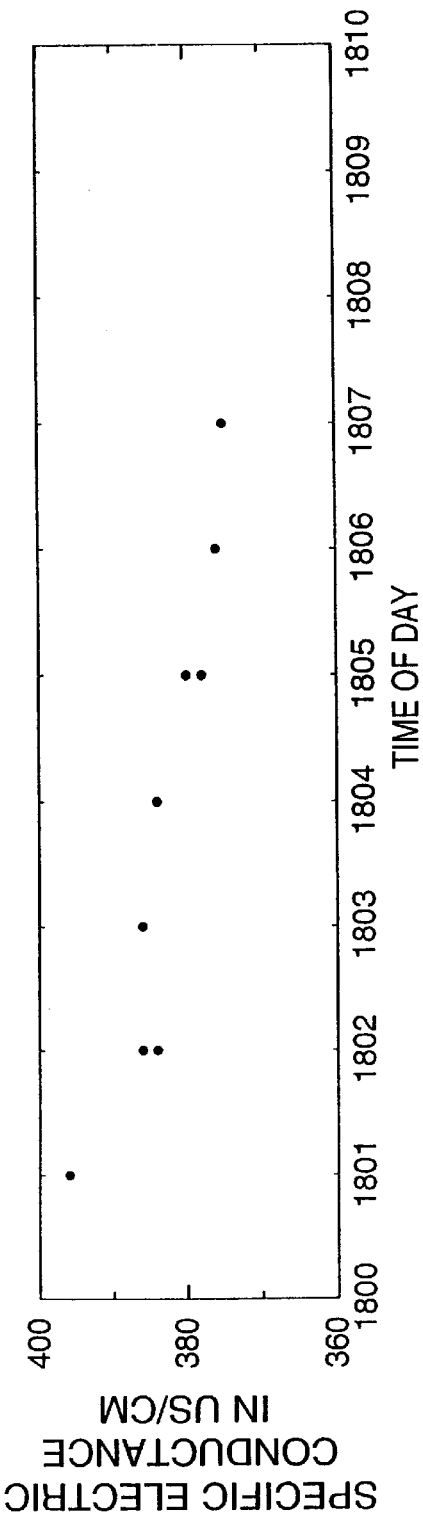
Figure 11E:
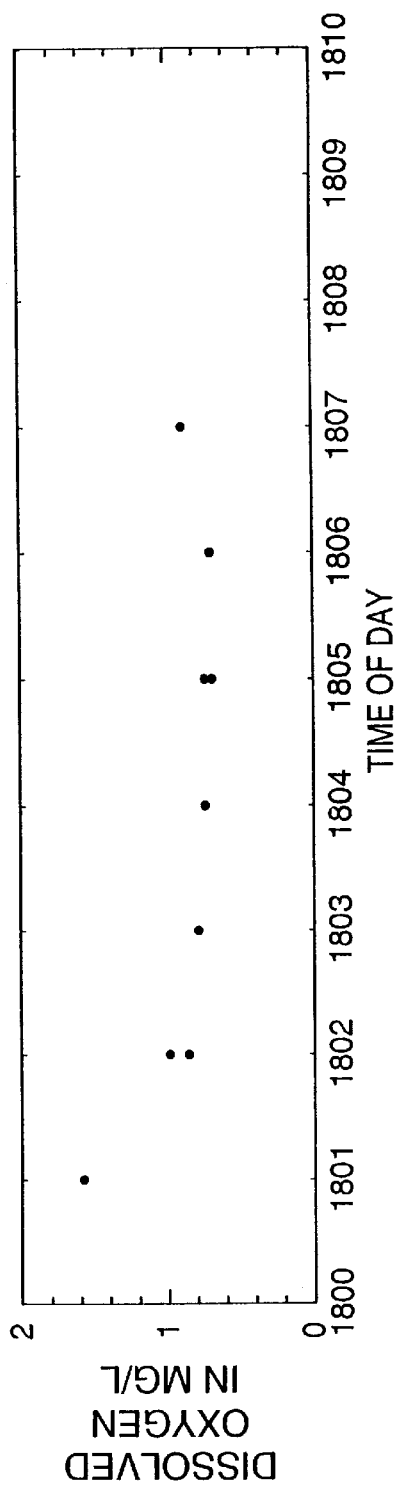
Figure 12A:
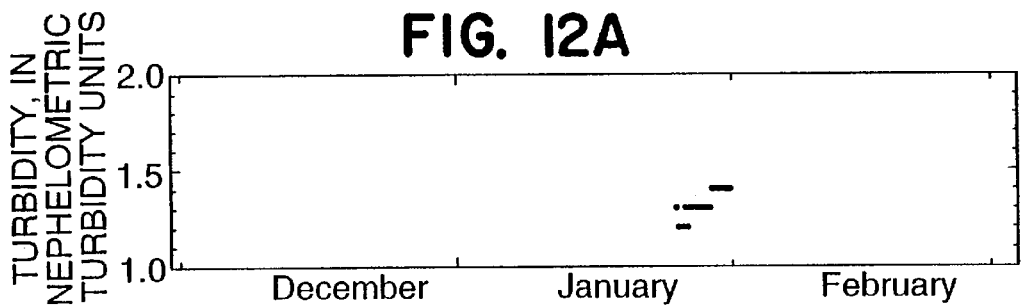
FIGS. 12A–12E are graphs showing water property and constituent measurements taken in the second working example of the present invention.
Figure 12B:
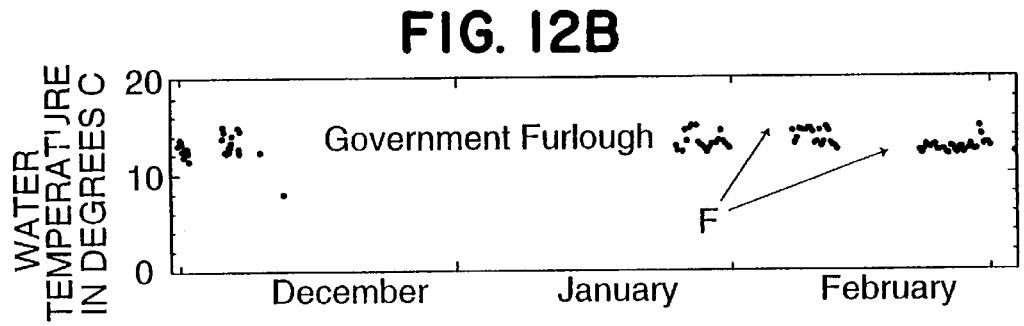
Figure 12C:
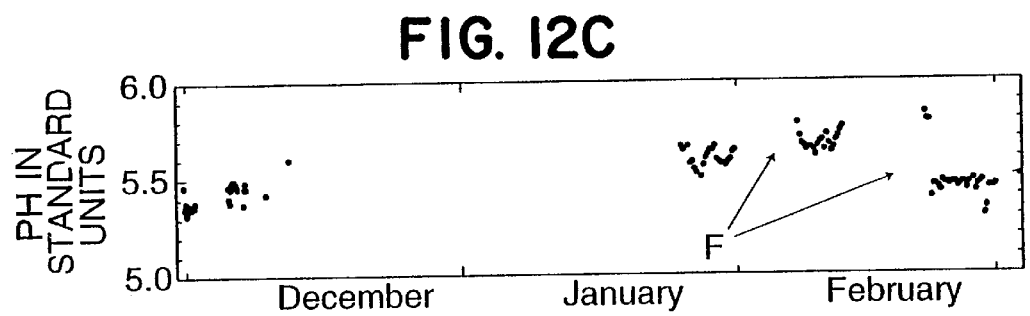
Figure 12D:
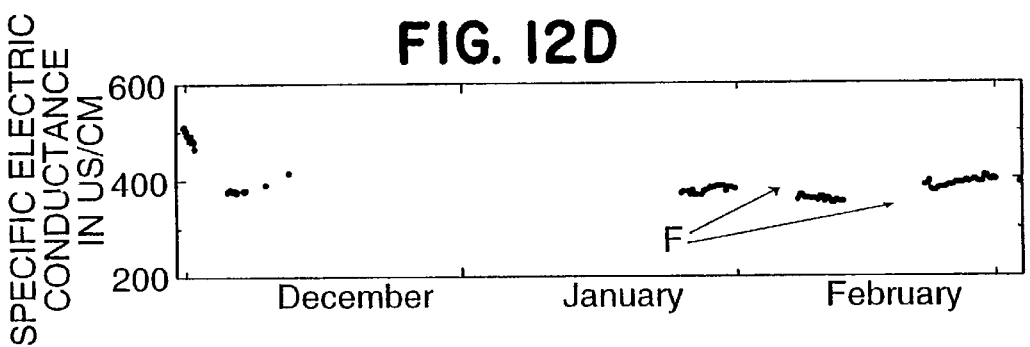
Figure 12E:
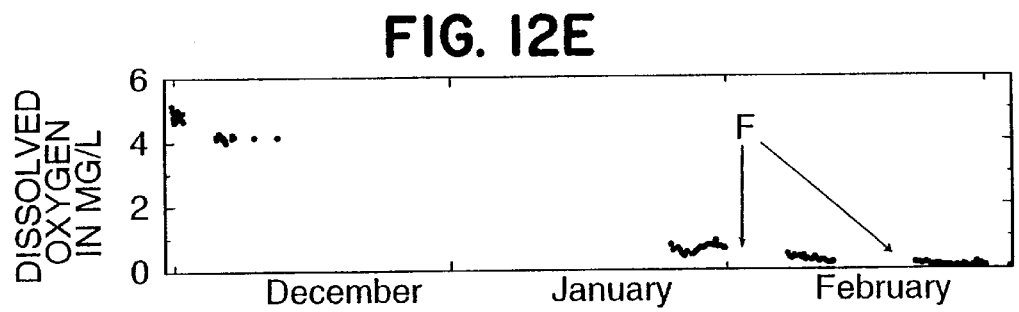

A second example of the process of the present invention, utilizing purge criteria based upon geochemical stability, was implemented at a USGS research site on Cape Cod, Mass. During purging, the water quality properties (turbidity, water temperature, pH, specific conductance, and dissolved oxygen) were monitored until the variance of the last five readings for each parameter was within a predetermined range around the average of the last five recorded values, as shown in FIG. 11. The process was performed using three electrical peristaltic pumps to sample three tubes in a multilevel sampling installation. A common set of water-quality monitoring instruments was used, with dedicated pumps sampling each port of the multilevel sampler sequentially and recording values under automated control. FIGS. 12A=12E are graphs showing ground water properties and constituents measurements of turbidity (FIGS. 12A), water temperature (FIG. 12B), pH (FIG. 12C), specific conductance (FIG. 12D), and dissolved oxygen (FIG. 12E), taken by the system. Overall, he system operated successfully throughout the testing period, however on two occasions the system was shut down because of equipment freezing, as shown by arrows F.

THIRD WORKING EXAMPLE

Figure 13A:
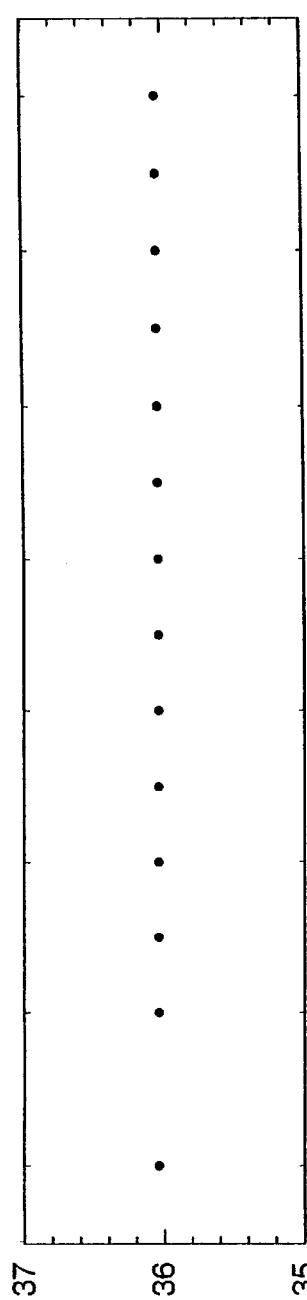
FIGS. 13A–13E are graphs showing purge values in a third working example of the present invention.
Figure 13B:
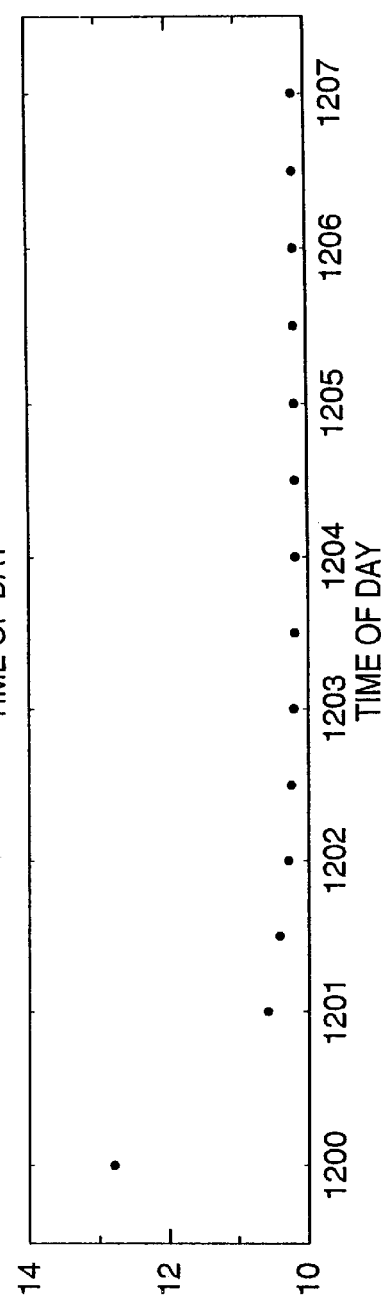
Figure 13C:
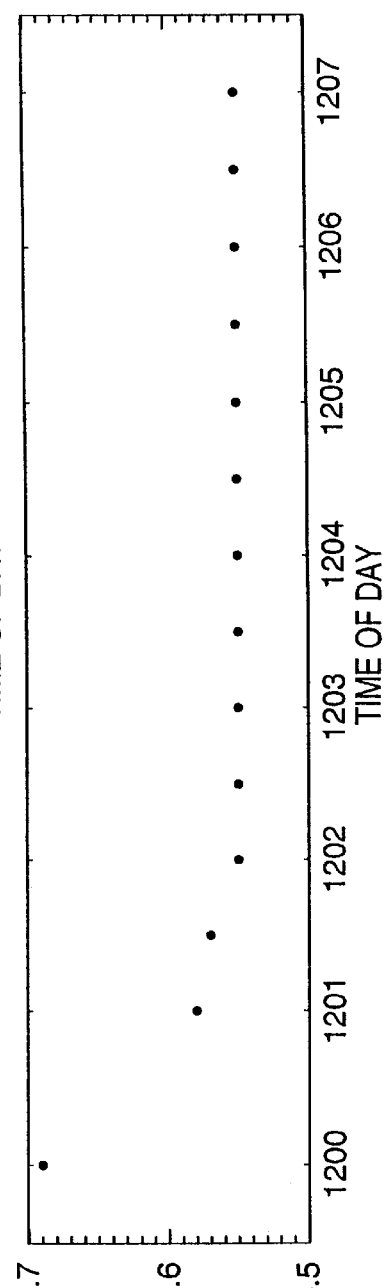
Figure 13D:
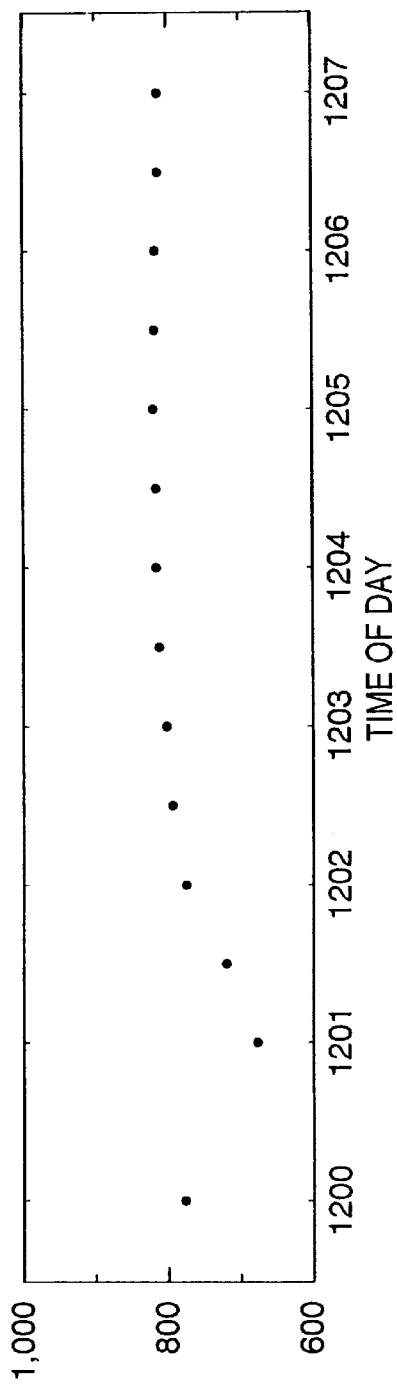
Figure 13E:
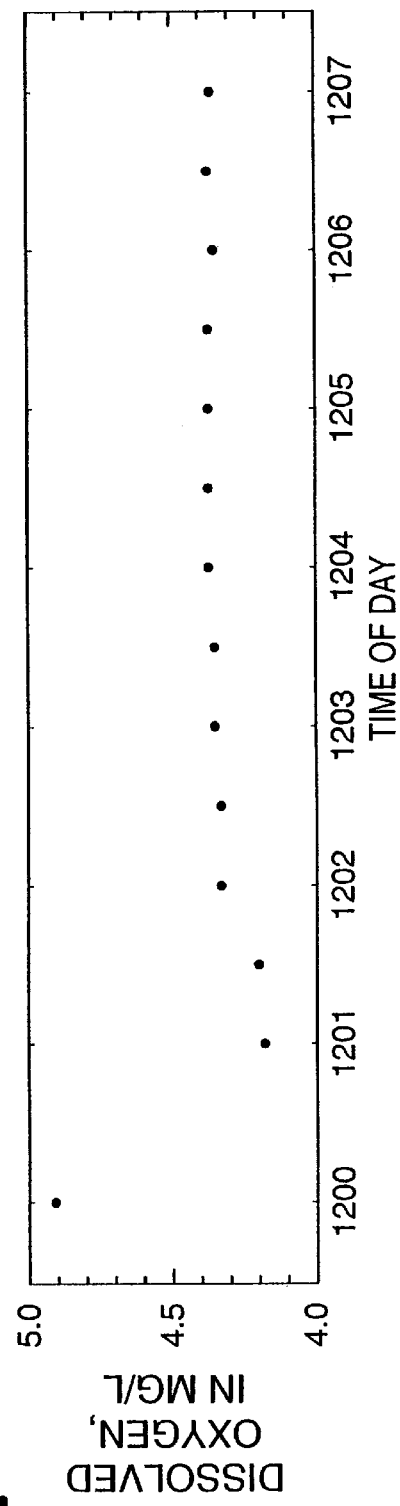
Figure 14D:
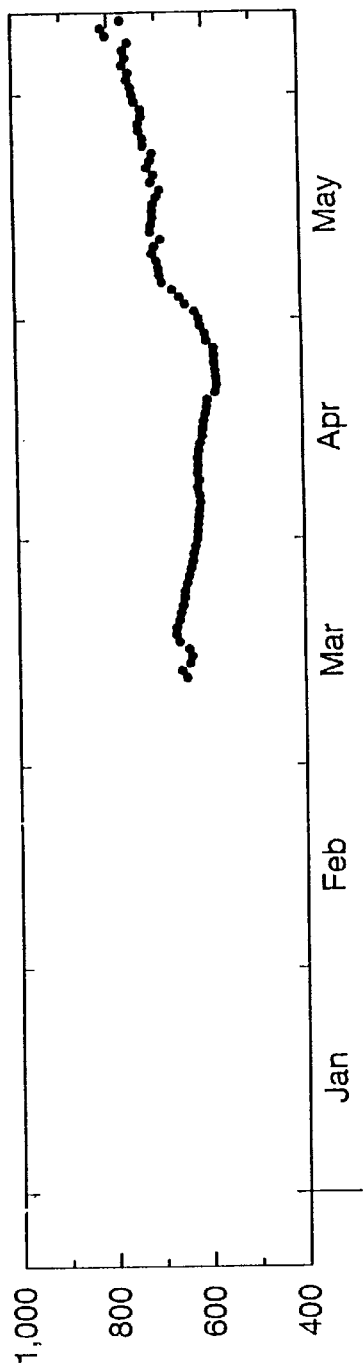
Figure 14E:
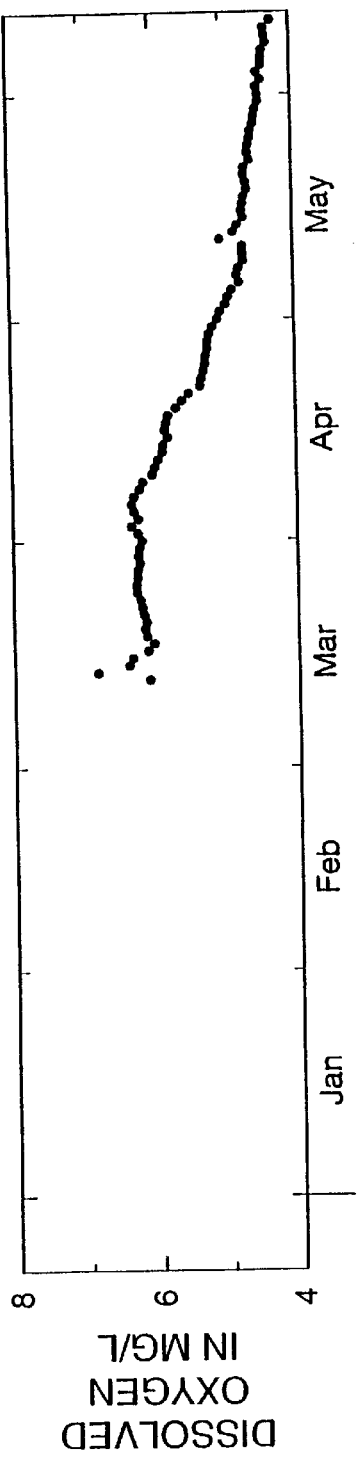

A third example of the present invention was successfully employed at a sampling site in Plymouth, Mass. Purging from a two-inch diameter well was performed until the purge criteria of evacuation of at least three borehole volumes of water was achieved, using an electrical submersible pump. During purging, the same water quality attributes were monitored to assure that geochemical stability had been obtained after the three borehole volumes had been pumped out. FIG. 13A shows the water level measurements obtained during the purging process; FIG. 13B shows the water temperature measurements obtained; FIG. 13C shows the pH measurements obtained; FIG. 13D shows the specific conductance measurements obtained; and FIG. 13E show the dissolved oxygen measurements obtained. FIGS. 14A–14E are graphs showing water quality measurements of water level (FIG. 14A), water temperature (FIG. 14B), pH (FIG. 14C), specific conductance (FIG. 14D), and dissolved oxygen (FIG. 14E) obtained during operation. Comparative manual measurements were not taken.

Other modifications to and variations of the invention will be apparent to those skilled in the art from the foregoing disclosure. Thus, while only certain embodiments of the invention have been specifically described herein, it will be apparent that numerous modifications may be made thereto without departing from the spirit and scope of the invention.

What is claimed is:

1. An automated method of unattended, continuous, real-time monitoring the quality of ground water at a sampling site, said method comprising the steps of:

(a) measuring the water level at the sampling site;

(b) calculating a minimum purge volume for the sampling site, based on the measured water level;

(c) purging at least the minimum purge volume from the sampling site;

(d) monitoring at least one of (i) a preselected water quality property of the water being purged from the sampling site, and (ii) a water quality constituent of the water being purged from the sampling site;

(e) comparing the monitored water quality property and water quality constituent with a selected purge criterion; and (f) recording the monitored water quality property and water quality constituent when the monitored water quality property and water quality constituent compare favorably with the selected purge criterion, wherein steps (d) and (e) are performed in accordance with a predetermined schedule and with a frequency sufficient to enable detection of a trend in measurement values of the at least one of the water quality property and the water quality constituent.

2. The method claimed in claim 1, wherein steps (b) through (f) are controlled by a computer program.

3. The method claimed in claim 2, wherein said computer program causes steps (b) through (f) to be performed when changes in water quality at the sampling site are expected to occur.

4. The method claimed in claim 2, wherein the computer program is adapted to be preempted by instructions, from an external source, for controlling steps (b) through (f).

5. The method claimed in claim 1, further comprising the step of:

(g) automatically storing in a memory the record of the water quality property and water quality constituent recorded in step (f).

6. The method claimed in claim 5, further comprising the step of:

(h) downloading the record of the stored water quality property and water quality constituent memory.

7. The method claimed in claim 1, further comprising the steps of:

(g) receiving a signal requesting transmission of the measurement value to a remote base station; and (h) transmitting the measurement value to the remote base station in response to the request signal.

8. The method claimed in claim 1, further comprising the steps of:

(g) sensing the status of present conditions at the sampling site; and (h) terminating at least one of steps (b) through (f) when step (g) indicates an error condition.

9. The method claimed in claim 8, further comprising the step of:

(i) transmitting a signal indicative of the error condition to a base station remote from the sampling site.

10. The method claimed in claim 9, wherein step (i) is performed automatically upon indication of the error condition.

11. The method claimed in claim 8, wherein the error condition includes at least one of low water level, insufficient power supply, equipment malfunction, and detection that the at least one of the water quality property and the water quality constituent obtained during step (d) lies outside a predetermined range.

12. The method claimed in claim 1, further comprising the steps of:

(g) automatically repeating step (d) to obtain a plurality of measurement values of the at least one of the water quality property and the water quality constituent over a predetermined interval of time; and (h) determining the degree to which the water quality at the sampling site has changed over the predetermined interval of time based on the plurality of measurement values.

13. The method claimed in claim 12, further comprising performing a repetition of step (c) before each repetition of step (d).

14. The method claimed in claim 12, wherein step (d) is repeated periodically in accordance with a predetermined sampling schedule throughout the predetermined interval of time.

15. The method claimed in claim 1, further comprising the step of:

(g) expelling from the sampling site water purged during step (c) to prevent contamination of unpurged water remaining at the sampling site.

16. The method claimed in claim 1, wherein the water quality property includes at least one of water temperate, specific conductance, pH, and turbidity.

17. The method claimed in claim 1, wherein the water quality constituent includes at least one of dissolved oxygen, dissolved ammonium, and dissolved nitrogen.

18. The method claimed in claim 1, wherein the sampling site includes a plurality of sampling locations, and steps (a)–(f) are repeated for each sampling location.

19. The method claimed in claim 1, wherein step (b) comprises calculating an amount of water to be purged from the sampling site to cause the at least one of the water quality property and the water quality constituent to be stabilized to within a predicted range.

20. The method claimed in claim 1, further comprising the steps of:

(g) activating a transmitter at a remote base station to request transmission of the measurement value to the remote base station; and (h) transmitting the measurement value to the remote base station in response to the request signal from the remote base station.

21. The method claimed in claim 1, further comprising:

(g) recording the monitored water quality property and water quality constituent during step (d).

22. An automated method of unattended, continuous, real-time monitoring of the quality of ground water at a sampling site, said method comprising the steps of:

(a) measuring the water level at the sampling site;

(b) calculating a minimum purge volume for the sampling site, based on the measured water level;

(c) purging at least the minimum purge volume from the sampling site;

(d) monitoring at least one of (i) a preselected water quality property of the water being purged from the sampling site, and (ii) a water quality constituent of the water being purged from the sampling site;

(e) comparing the monitored water quality property and water quality constituent with a selected purge criterion; and (f) recording the monitored water quality property and water quality constituent when the monitored water quality property and water quality constituent compare favorably with the selected purge criterion, wherein steps (d) and (e) are performed in accordance with a predetermined schedule and with a frequently sufficient to enable detection of an abrupt change in the obtained measurement values.

23. The method claimed in claim 22, wherein steps (b) through (f) are controlled by a computer program.

24. The method claimed in claim 23, wherein said computer program causes steps (b) through (f) to be performed when changes in water quality at the sampling site are expected to occur.

25. The method claimed in claim 23, wherein the computer program is adapted to be preempted by instructions, from an external source, for controlling steps (b) through (f).

26. The method claimed in claim 22, further comprising the step of:

(g) automatically storing in a memory the record of the water quality property and the water quality constituent recorded in step (f).

27. The method claimed in claim 26, further comprising the step of:

(h) downloading the record of the stored water quality property and water quality constituent from the memory.

28. The method claimed in claim 22, further comprising the steps of:

(g) receiving a signal requesting transmission of the measurement value to the remote base station; and (h) transmitting the measurement value to the remote base station in response to the request signal.

29. The method claimed in claim 22, further comprising the steps of:

(g) sensing the status of preselected conditions at the sampling site; and (h) terminating at least one of steps (b) through (f) when step (g) indicates an error condition.

30. The method claimed in claim 29, further comprising the step of:

(i) transmitting a signal indicative of the error condition to a base station remote from the sampling site.

31. The method claimed in claim 30, wherein step (i) is performed automatically upon indication of the error condition.

32. The method claimed in claim 29, wherein the error condition includes at least one of low water level, insufficient power supply, equipment malfunction, and detection that the at least one of the water quality property and the water quality constituent obtained during step (d) lies outside a predetermined range.

33. The method claimed in claim 22, further comprising the steps of:

(g) automatically repeating step (d) to obtain a plurality of measurement values of the at least one of the water quality property and the water quality constituent over a predetermined interval of time; and (h) determining the degree to which the water quality at the sampling site has changed over the predetermined interval of time based on the plurality of measurement values.

34. The method claimed in claim 33, further comprising performing a repetition of step (c) before each repetition of step (d).

35. The method claimed in claim 33, wherein step (d) is repeated periodically in accordance with a predetermined sampling schedule throughout the predetermined interval of time.

36. The method claimed in claim 22, further comprising the step of:

(g) expelling from the sampling site water purged during step (c) to prevent contamination of unpurged water remaining at the sampling site.

37. The method claimed in claim 22, wherein the water quality property includes at least one of water temperature, specific conductance, pH, and turbidity.

38. The method claimed in claim 22, wherein the water quality constituent includes at least one of dissolved oxygen, dissolved ammonium, and dissolved nitrogen.

39. The method claimed in claim 22, wherein the sampling site includes a plurality of sampling locations, and steps (a)–(f) are repeated for each sampling location.

40. The method claimed in claim 22, wherein step (b) comprises calculating an amount of water to be purged from the sampling site to cause the at least one of the water quality property and the water quality constituent to be stabilized to within a predetermined range.

41. The method claimed in claim 22, further comprising the steps of:
   (g) activating a transmitter at a remote base station to request transmission of the measurement value to the remote base station; and
   (h) transmitting the measurement value to the remote base station in response to the request signal from the remote base station.

42. The method claimed in claim 22, further comprising:
   (g) recording the monitored water quality property and water quality constituent during step (d).

43. Apparatus for monitoring the quality of ground water in a sampling site, said apparatus comprising:
   a transducer for measuring the water level in the sampling site;
   a pump for purging water from the sampling site;
   a sensor for monitoring at least one of (i) a preselected water quality property of the water being purged from the sampling site, and (ii) a water quality constituent of the water being purged from the sampling site; and
   a controller for causing unattended, continuous, real-time monitoring of the ground water quality by (i) calculating a minimum purge volume for the sampling site, based on the measured water level (ii) controlling the pump to purge at least the minimum purge volume from the sampling site, (iii) controlling the sensor to monitor the at least one of the preselected water quality property and water quality constituent, (iv) comparing the monitored water quality property and water quality constituent with a selected purge criterion, and (v) recording the monitored water quality property and water quality constituent when the monitored water quality property and water quality constituent compare favorably with the selected purge criterion, said controller causing such monitoring and comparing in accordance with a predetermined schedule and with a frequency sufficient to enable detecting of a trend in measurement values of the at least one of the water quality property and the water qualify constituent.

44. Apparatus for monitoring quality of ground water in sampling site, said apparatus comprising:
   a transducer for measuring the water level in the sampling site;
   a pump for purging water from the sampling site;
   a sensor for monitoring at least one of (i) a preselected water quality property of the water being purged from the sampling site, and (ii) a water quality constituent of the water being purged from the sampling site; and
   a controller for causing unattended, continuous, real-time monitoring of the ground water quality by (i) calculating a minimum purge volume for the sampling site, based on the measured water level, (ii) controlling the pump to purge at least the minimum purge volume from the sampling site, (iii) controlling the sensor to monitor the at least one of the preselected water quality property and water quality constituent, (iv) comparing the monitored water quality property and water quality constituent with a selected purge criterion, and (v) recording the monitored water quality properly and water quality constituent when the monitored water quality property and water quality constituent compare favorably with the selected purge criterion, said controller causing such monitoring and comprising in accordance with a predetermined schedule and with a frequency sufficient to enable detection of an abrupt change in the obtained measurement values.

45. Apparatus for monitoring quality of ground water in a well, said apparatus comprising:
   a transducer for measuring the water level in the well;
   a pump for purging water from the well;
   a sensor for monitoring at least one of (i) a preselected water quality property of the water being purged from the well, and (ii) a water quality constituent of the water being purged from the well; and
   a controller for causing unattended, continuous, real-time monitoring of the ground water quality by (i) calculating a minimum purge volume for the well, based on the measured water level, (ii) controlling the pump to purge at least the minimum purge volume from the well, (iii) controlling the sensor to monitor the at least one of the preselected water quality property and water quality constituent, (iv) comparing the monitored water quality property and water quality constituent with a selected purge criterion, and (v) recording the monitored water quality property and water quality constituent when the monitored water quality property and water quality constituent compare favorably with the selected purge criterion, said controller causing such monitoring and comparing in accordance with a predetermined schedule and with a frequency sufficient to enable detection of an abrupt change in the obtained measurement values.

46. Apparatus for monitoring the quality of ground water in a well said apparatus comprising:
   a transducer for measuring the water level in the well;
   a pump for purging water from the well;
   a sensor for monitoring at least one of (i) a preselected water quality property of the water being purged from the well, and (ii) a water quality constituent of the water being purged from the well; and
   a controller for causing unattended, continuous, real-time monitoring of the ground water quality by (i) calculating a minimum purge volume for the well, based on the measured water level, (ii) controlling the pump to purge at least the minimum purge volume from the well, (iii) controlling the sensor to monitor the at least one of the preselected water quality property and water quality constituent, (iv) comparing the monitored water quality property and water quality constituent with a selected purge criterion, and (v) recording the monitored water quality property and water quality constituent when the monitored water quality property and water quality constituent compare favorably with the selected purge criterion, said controller causing such monitoring and comparing in accordance with a predetermined schedule and with a frequency sufficient to enable detection of a trend in measurement values of the at least one of the water quality property and the water quality constituent.

* * * * *